United States Patent
Weyand et al.

(10) Patent No.: US 9,511,086 B2
(45) Date of Patent: Dec. 6, 2016

(54) METHOD FOR IMPROVING IMMUNE SYSTEM FUNCTION BY ADMINISTERING AGENTS THAT INHIBIT DNA-DEPENDENT PROTEIN KINASE-DIRECTED APOPTOSIS

(75) Inventors: Cornelia M. Weyand, Stanford, CA (US); Jörg J. Goronzy, Palo Alto, CA (US); Lan Shao, Stanford, CA (US)

(73) Assignees: The Board of Trustees of the Leland Stanford Junior University, Stanford, CA (US); Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/205,001

(22) Filed: Aug. 8, 2011

(65) Prior Publication Data

US 2012/0039867 A1 Feb. 16, 2012

Related U.S. Application Data

(60) Provisional application No. 61/372,829, filed on Aug. 11, 2010.

(51) Int. Cl.
| | |
|---|---|
| *A61K 31/7088* | (2006.01) |
| *A61K 31/7105* | (2006.01) |
| *A61K 31/711* | (2006.01) |
| *G01N 33/50* | (2006.01) |
| *A61K 38/00* | (2006.01) |

(52) U.S. Cl.
CPC ......... *A61K 31/7088* (2013.01); *A61K 31/711* (2013.01); *A61K 31/7105* (2013.01); *G01N 33/5008* (2013.01); *A61K 38/00* (2013.01); *G01N 2800/102* (2013.01)

(58) Field of Classification Search
CPC ............ A61K 31/7088; A61K 31/7105; A61K 31/711; A61K 31/12
See application file for complete search history.

(56) References Cited

U.S. PATENT DOCUMENTS

2007/0003531 A1* 1/2007 Mukherji et al. .......... 424/93.21

OTHER PUBLICATIONS

Shao L et al. Deficiency of the DNA repair enzyme ATM in rheumatoid arthirtis. J. Exp. Med. 206 (6): 1435-1449, 2009.*
Christmann et al. Mechanisms of DNA repair: an update. Toxicology 193: 3-34, 2003.*
Scarpaci et al. DNA damage recognition and repair capacities in human naive and memory T cells from peripheral blood of young and elderly subjects. Mechanisms of Aging. 124:517-524, 2003.*
Luo et al. Gene of DNA-dependent protein kinase catalytic subunit in chronic myeloid leukemia. Journal of experimental hematology. 15(2):248-52, 2007—Abstract only.*
Lin et al. Increased apoptosis of peripheral blood T cells following allogeneic hematopoietic cell transplantation. Blood. 95(12):3832-3839, 2000.*
Shao et al. Deficiency of the DNA repair enzyme ATM in rheumatoid arthritis. Journal of Experimental Medicine 206(6):1435-1449, 2009.*
Maurer et al. Evidence for the presence of activated CD4 T cells with a naive phenotype in the peripheral blood of patients with rheumatoid arthritis. Clinical Experimental Immunology. 87:429-434, 1992.*
Park et al. Involvement of DNA-dependent kinase in regulation of stress-induced JNK activation. DNA and Cell Biology. 20(10):637-645, 2001.*
Shrivastav et al. Regulation of DNA double strand break repair pathway choice. Cell Research. 18:134-147, 2008.*
Maurer et al. Evidence for the presence of activated CD4 T cells with naive phenotype in the peripheral blood of patients with rheumatoid arthritis. Clinical Experimental Immunology. 1992; 87:429-434.*
Christmann et al. Mechanisms of human DNA repair: an update. Toxicology. 2003; 193:3-34.*
Sedelnikova et al. Delayed kinetics of DNA double-strand break processing in normal and pathological aging. Aging Cell. 2008; 7:89-100.*
Shao et al. Deficient of the DNA repair enzyme ATM in rheumatoid arthritis. Journal of Experimental Medicine. 2009; 60:1435-1449.*
Kashishian et al, (2003), Molecular Cancer Therapeutics, 2 (12):1257-1264.*
Shao; et al., "DNA-dependent protein kinase catalytic subunit mediates T-cell loss in rheumatoid arthritis", EMBO Molecular Medicine (2010), 2:415-427.

* cited by examiner

*Primary Examiner* — Prema Mertz
(74) *Attorney, Agent, or Firm* — Otto C. Guedelhoefer; Bozicevic, Field & Francis LLP

(57) ABSTRACT

Methods and compositions for improving immune system function are provided. These methods find particular use in improving immune system function in individuals with a condition in which naïve lymphocytes comprise elevated amounts of DNA double strand breaks (DSB), for example, individuals with Rheumatoid Arthritis, individuals that have received a bone marrow transplant, or elderly individuals, e.g. individuals that are 50 or more years old. Also provided are methods and compositions for screening for novel compounds that will improve immune system function in such individuals.

14 Claims, 8 Drawing Sheets

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
aggaattccc agtaagtgcg                                                    20

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2
gcctcactaa accatccaa                                                     19

<210> SEQ ID NO 3
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 3
```
ctttgtcgtg tggagggaa                                                    19

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
cacaacgggg ttcagaagtt                                                   20

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
ggacgacctc aacgcacagt a                                                 21

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
ggcaggagtc ccatgatgag a                                                 21

<210> SEQ ID NO 7
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 7
cctgggaaga aggcgcg                                                      17

<210> SEQ ID NO 8
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 8
tcaggttcct gtgcagaag                                                    19

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
acgcttacta tgcaaggagg g                                                 21

<210> SEQ ID NO 10
<211> LENGTH: 21
<212> TYPE: DNA
<213> ORGANISM: Artificial Sequence

```
<220> FEATURE:
<223> OTHER INFORMATION: synthetic oligonucleotide

<400> SEQUENCE: 10
ggtcttcggc tgcttggtaa t                                              21

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
ctgcacaacc ttgctttgaa                                                20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
caagggcctg acagagaaag                                                20

<210> SEQ ID NO 13
<211> LENGTH: 16
<212> TYPE: PRT
<213> ORGANISM: Artificial Sequence
<220> FEATURE:
<223> OTHER INFORMATION: synthetic peptide

<400> SEQUENCE: 13

Arg Gln Ile Lys Ile Trp Phe Gln Asn Arg Arg Met Lys Trp Lys Lys
 1               5                  10                  15
```

METHOD FOR IMPROVING IMMUNE SYSTEM FUNCTION BY ADMINISTERING AGENTS THAT INHIBIT DNA-DEPENDENT PROTEIN KINASE-DIRECTED APOPTOSIS

CROSS REFERENCE TO RELATED APPLICATIONS

Pursuant to 35 U.S.C. §119 (e), this application claims priority to the filing date of U.S. Provisional Patent Application Ser. No. 61/372,829, filed Aug. 11, 2010, the disclosure of which is herein incorporated by reference.

GOVERNMENT RIGHTS

This invention was made with Government support under contracts AI057266, AI044142, and AR042527 awarded by the National Institutes of Health. The Government has certain rights in the invention.

FIELD OF THE INVENTION

This invention pertains to the use of agents that inhibit DNA-PKcs-directed apoptosis and promote mechanisms of Double Strand Break Repair to improve immune system function in patients with conditions characterized by a premature senescence of the immune system.

BACKGROUND OF THE INVENTION

In diseases characterized by chronic immune responses, unprimed T and B lymphocytes are under excessive replication pressure, resulting in age-inappropriate telomeric shortening, the accumulation of DNA damage, and ultimately, increased rates of apoptosis in these lymphocytes. Increased attrition of these naïve lymphocytes imposes lymphopenia-induced proliferation, leading to premature immunosenescence and an autoimmune-biased lymphocyte repertoire. For example, in Rheumatoid Arthritis (RA), an autoimmune disease characterized by synovial inflammation and destruction of the joint architecture, naïve CD4+ T cells accumulate DNA double strand breaks and demonstrate an increased susceptibility to apoptosis, resulting in an accumulation of pro-inflammatory T-effector cell populations and loss of tolerance to neo-antigens. Restoration of DNA repair mechanisms in these naïve lymphocytes, either by promoting DNA double strand break repair (DSBR) or by preventing apoptosis until the cell's DSBR machinery can repair DNA damage, thus emerges as an important therapeutic approach in these diseases. The present invention addresses these issues.

SUMMARY OF THE INVENTION

Methods and compositions for improving immune system function are provided. These methods find a number of uses, such as improving immune system function in individuals with a condition in which naïve lymphocytes comprise elevated amounts of chromosomal DNA double strand breaks (DSB), e.g., in individuals with Rheumatoid Arthritis, in individuals that have received a bone marrow transplant, or in older individuals, e.g. individuals that are about 50 years old or older. Also provided are methods and compositions for screening for novel compounds that will improve immune system function in such individuals.

In some aspects of the invention, a method is provided for improving immune system function in an individual with a condition in which naïve lymphocytes comprise elevated amounts of DNA double strand breaks (DSB), i.e. amounts of DSBs that are greater than in a normal control, e.g. an individual that is unaffected by the condition; or, when the individual that has an elevated number of DSBs due to older age, a healthy individual under the age of 40. In these methods, naïve lymphocytes from the individual are contacted with an effective amount of an agent that inhibits DNA-PKcs-directed apoptosis and/or an effective amount of an agent that promotes double strand break repair (DSBR). In some embodiments, the agent that inhibits DNA-PKcs-directed apoptosis is an agent that inhibits the activity of DNA-PKcs, JNK1, JNK2, JNK3, BIM, or BIF-1. In some embodiments, the agent that promotes DSBR is an agent that promotes non-homologous end-joining (NHEJ). In some such embodiments, the agent promotes the activity of Ku70, Ku80, XRCC4, DNA ligase IV, or XLF. In some embodiments, the agent that promotes DSBR is an agent that promotes homology-directed repair (HDR). In some such embodiments, the agent promotes the activity of MRE11, RAD50, NBS1, RAD51, RAD52, BRCA1 or BRCA2. In some embodiments, the naïve lymphocytes are naïve CD4+ T cells. In some embodiments, the naïve lymphocytes are mature B lymphocytes. In some embodiments, the naïve lymphocytes are hematopoietic progenitor cells. In some embodiments, the agent is administered to the lymphocytes in vivo. In other embodiments, the agent is administered to the lymphocytes ex vivo.

In some embodiments, the accumulation of double strand breaks (DSBs) in naïve lymphocytes of the individual is reduced. In some embodiments, the rate of apoptosis of naïve lymphocytes is reduced. In some embodiments, the viability of the lymphocytes is increased. In some embodiments, the diversity of the lymphocytes is increased. In some embodiments, the method further comprises the step of monitoring lymphocyte viability and/or diversity and/or function in the individual. In some embodiments, the condition is Rheumatoid Arthritis. In some such embodiments, the agent is co-administered with a therapy to treat the condition. In some embodiments, the condition is a bone marrow transplant. In some such embodiments, the agent is co-administered with a therapy to prevent susceptibility to infection. In some embodiments, the condition is older age, e.g. 50 years of age.

In some aspects of the invention, a method is provided for reducing T lymphocyte apoptosis in an individual with a condition in which naïve T lymphocytes comprise elevated amounts of DNA double strand breaks (DSB) relative to a normal control. In such methods, T lymphocytes from the individual are contacted with an effective amount of an agent that inhibits DNA-PKcs-directed apoptosis and/or and an agent that promotes double strand break repair (DSBR). In some embodiments, the agent that inhibits DNA-PKcs-directed apoptosis is an agent that inhibits the activity of DNA-PKcs, JNK1, JNK2, JNK3, BIM, or BIF-1. In some embodiments, the agent that promotes DSBR is an agent that promotes non-homologous end-joining (NHEJ). In some such embodiments, the agent promotes the activity of Ku70, Ku80, XRCC4, DNA ligase IV, or XLF. In some embodiments, the agent that promotes DSBR is an agent that promotes homology-directed repair (HDR). In some such embodiments, the agent promotes the activity of MRE11, RAD50, NBS1, RAD51, RAD52, BRCA1 or BRCA2. In some embodiments, the T lymphocytes are naïve CD4+ T cells. In some embodiments, the agent is administered to the lymphocytes in vivo. In other embodiments, the agent is administered to the lymphocytes ex vivo. In some embodiments, the agent is co-administered with a therapy to treat the condition. In some embodiments, the condition is Rheumatoid Arthritis.

In some embodiments, the method further comprises the step of monitoring lymphocyte viability and/or diversity and/or function in the individual. In some embodiments, lymphocyte viability and/or diversity and/or function is monitored by measuring the number of naïve lymphocytes in the blood, the lymph nodes, the spleen, and/or the bone marrow of the individual prior to and subsequent to contacting the naïve lymphocytes with the agent, wherein elevated numbers of naïve lymphocytes subsequent to contact with the agent relative to prior to contact with the agent is prognostic of an improved immune system function. In some such embodiments, the agent is co-administered with a therapy to treat the condition. In some such embodiments, the therapy is a therapy to prevent susceptibility to infection.

In some aspects of the invention, methods are provided for screening candidate agents for activity in improving immune system function in an individual with a condition in which lymphocytes have elevated amounts of DNA double strand breaks (DSB) relative to a normal control. In these methods, cells with elevated numbers of DSBs are contacted with a candidate agent and output parameters, e.g. viability and/or function of the cells, are monitored, i.e. compared to the output parameters of cells with elevated numbers of DSBs that were not contacted with the candidate agent, where alterations in output parameters, e.g. enhanced cell viability and/or function, in the cells contacted with the candidate agent indicates that the candidate agent will improve immune function in an individual with a condition in which lymphocytes have elevated amounts of DNA double strand breaks (DSB) relative to a normal control. In some embodiments, the condition is Rheumatoid Arthritis.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

Representative data from one patient and one control are shown. (D) Cell apoptosis from 3 control and 3 RA samples are presented as mean±SEM.

Figure 7:
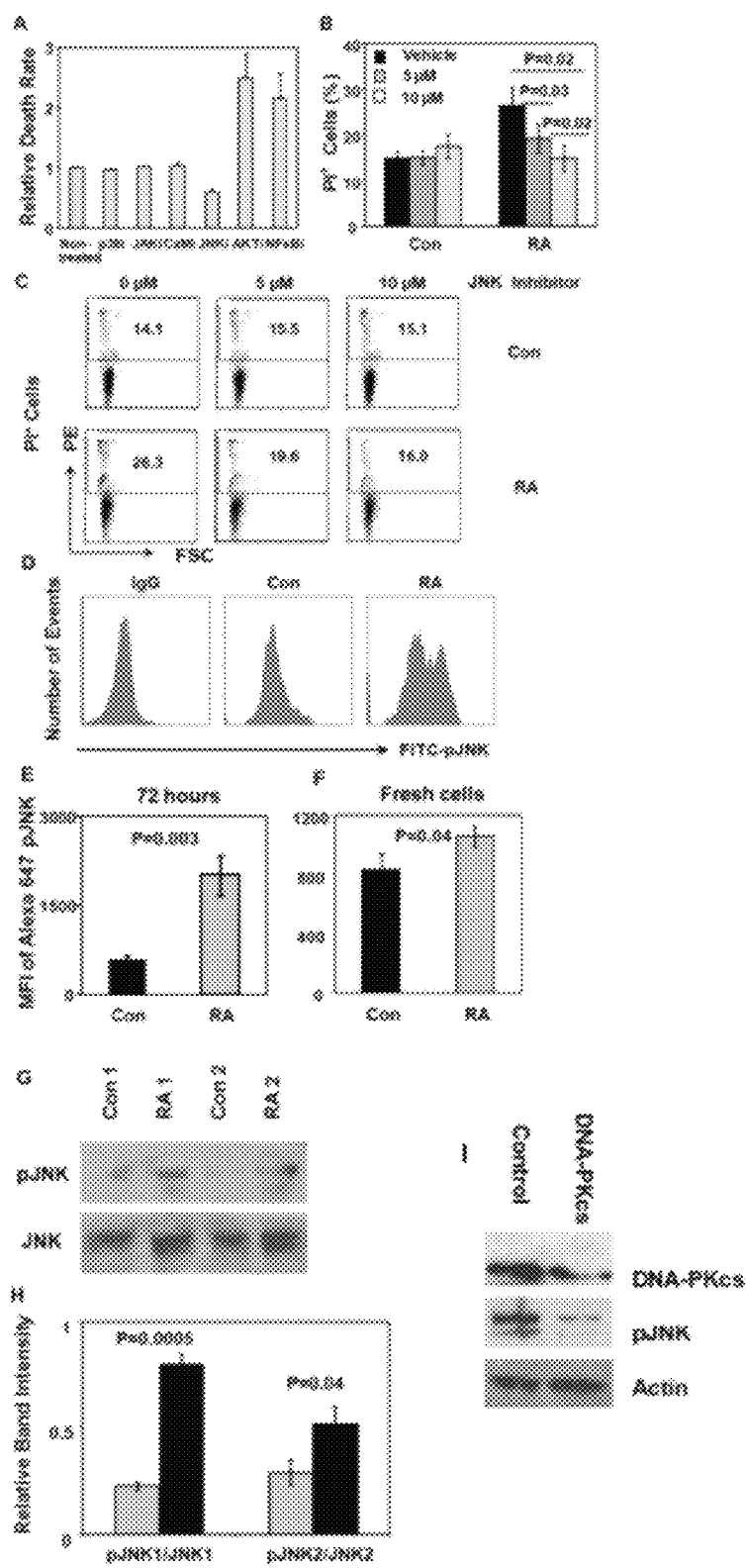

FIG. 7. Spontaneous apoptosis of RA CD4+ T cells is mediated through the JNK pathway and JNK is upregulated by DNA-PKcs. (A) CD4+CD45RO– T cells were isolated and cultured in the presence of the indicated enzyme inhibitors for 24 h. T-cell apoptosis was quantified through flow cytometry staining for PI. (B) Cells were maintained in culture without stimulation for 48 h and then were treated with the JNK inhibitor. PI-positive T cells were measured after 24 h of treatment with the JNK inhibitor II (5 µM or 10 µM) or vehicle. Frequencies of apoptotic T cells from 6 controls and 7 RA patients are presented as mean±SEM. (C) Representative flow cytometry results from one control and one patient. (D) Flow cytometry analysis of phosphorylated JNK levels in control and RA T cells after culturing without mitogenic stimulation for 72 h. Representative data from one patient and one control are presented. (E) Expression of pJNK protein in n=6 RA and n=6 control samples at 72 h is given as MFI of FITC-pJNK. (F) Flow cytometry analysis of phosphorylated JNK levels in freshly isolated control and RA naïve CD4 T cells. Expression of pJNK protein in n=7 RA and n=7 control samples at day 0 is given as MFI of FITC-pJNK. (G) Quantification of JNK and pJNK protein expression at 72 h by Western blotting. (H) Relative expression levels of pJNK were quantified by measuring band intensities adjusted by total JNK in 6 RA patients and 6 control donors. Data are presented as mean±SEM. (I) CD4+CD45RO– T cells were purified from RA donors and transfected with control or DNA-PKcs-specific siRNA oligonucleotides by nucleofection. Twenty-four hours after transfection, DNA-PKcs and pJNK protein levels were detected by Western blotting. A representative blot from three independent experiments is shown.

Figure 8:
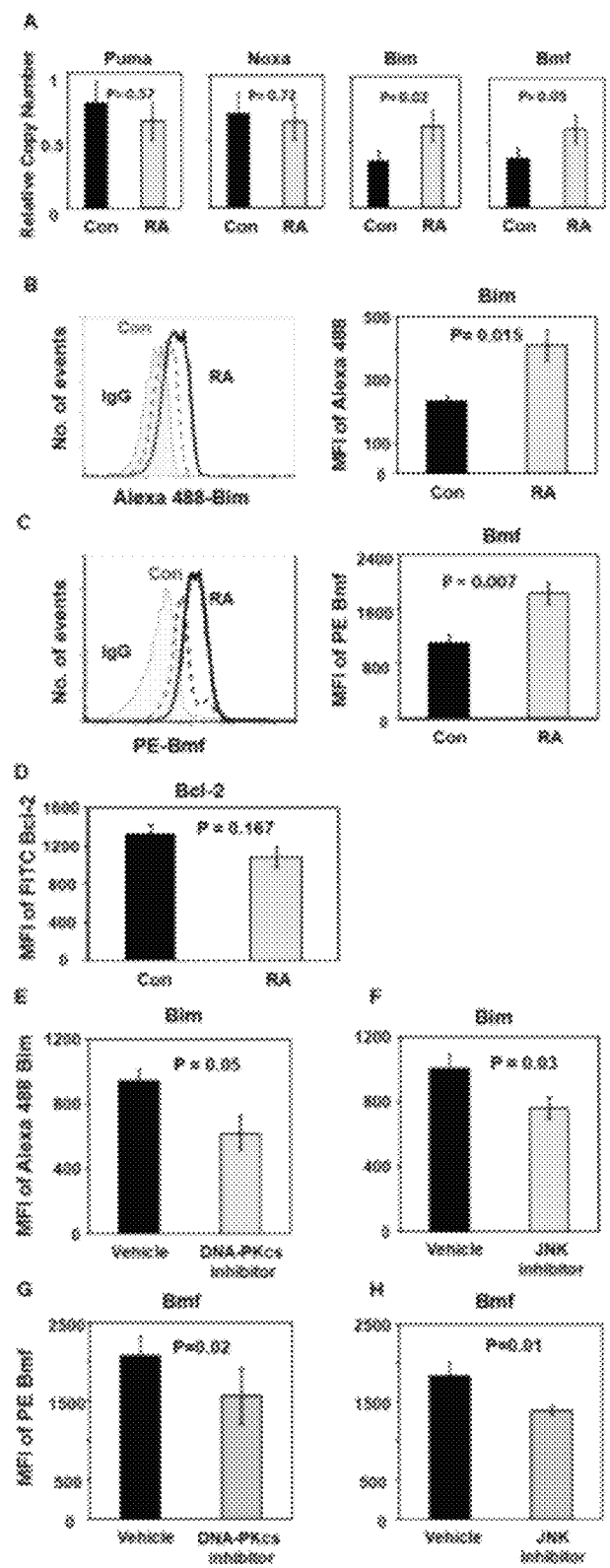

FIG. 8. The DNA-PKcs-JNK pathway upregulates the apoptogenic molecules Bim and Bmf in RA CD4+ T cells. CD4+CD45RO– T cells were isolated from the peripheral blood of 6 controls and 6 RA patients. Cells were maintained in culture without mitogenic stimulation for 72 h. (A) Puma, Noxa, Bim and Bmf transcript levels in freshly isolated cells were quantified by qPCR. Data are presented as mean±SEM. (B) Flow cytometry analysis of Bim levels in control and RA naïve T cells after 72 h of culture. Expression of Bim protein in n=5 RA and n=5 controls samples is given as MFI of Alexa Fluor 488 Bim. (C) Flow cytometry analysis of Bmf levels in control and RA naïve T cells. Expression of Bmf protein in n=6 RA and n=4 controls samples is given as MFI of PE Bmf. (D) Bcl-2 protein levels were analyzed by flow cytometry. Expression of Bcl-2 protein in n=6 RA and n=6 control samples is given as MFI of FITC Bcl-2. (E) Bim protein level in the absence and presence of the DNA-PKcs inhibitor were analyzed by flow cytometry in samples from 4 RA patients. (F) Flow cytometry analysis of Bim levels after treatment with the JNK inhibitor II or vehicle in naïve T cells from 6 RA patients. Results are presented as MFI±SEM. Flow cytometry analysis of Bmf protein expression in T cells from 3 RA patients in the absence and presence of the DNA-PKcs inhibitor II (G) or the JNK inhibitor II (H). Results are presented as MFI±SEM.

DETAILED DESCRIPTION OF THE INVENTION

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Methods and compositions for improving immune system function are provided. These methods find particular use in improving immune system function in patients with a condition in which naïve lymphocytes have elevated amounts of DNA double strand breaks (DSB), for example, patients with Rheumatoid Arthritis, patients that have received a bone marrow transplant, or elderly patients. These and other objects, advantages, and features of the invention will become apparent to those persons skilled in the art upon reading the details of the compositions and methods as more fully described below.

By "double strand breaks" or "DSBs", it is meant damaged genomic DNA in which both strands in the double helix are severed. Cells with elevated amounts of DSBs have about 1.5-fold more DSBs, i.e. 1.5-fold, 2-fold, 2.5-fold, 3-fold, 4-fold, 5-fold, 6-fold, 7-fold, 8-fold, 10-fold or more DSBs, than normal cells, e.g. cells in which DSBs have not been experimentally induced, or naïve lymphocytes from individuals unaffected by a condition characterized by an immune system comprising lymphocytes with elevated levels of DSBs.

By "double-strand break repair" or "DSBR", it is meant the mechanisms by which a cell identifies and corrects double strand breaks in its DNA, e.g. non-homologous end joining (NHEJ), and homology-directed repair (HDR). By "an agent that promotes DSBR", it is meant an agent that has activity in promoting DSBR. The DSBR activity of an agent can be determined by assessing the accumulation of double strand breaks (DSBs) in a cell following the addition (e.g. gain of function, e.g. by overexpression) and/or removal (e.g., loss of function, e.g. by knockout or knockdown) of that agent as known in the art and discussed in greater detail below.

By "non-homologous end joining" or NHEJ", it is meant the mechanism by which a cell identifies and corrects double strand breaks in its DNA that relies upon the alignment and ligation of double strand break (DSB) termini. Without wishing to be bound by theory, it is believed that in this process, the Ku70/Ku80 protein binds to the ends of the DSB and recruits DNA-PKcs. DNA-PKcs in turn recruits and activates the protein Artemis, which is responsible for processing DNA ends before XRCC4, DNA ligase IV, and XLF/Cernunnos facilitate the final ligation step. NHEJ is the major route of repair in the $G_0/G_1$ phases of the cell cycle. An agent that promotes NHEJ is an agent that promotes the activity of the aforementioned pathway, e.g. by promoting the activity of the aforementioned proteins, as will be discussed in greater detail below and as is understood in the art.

By "homology directed repair", "HDR", "homologous recombination", or "HR", it is meant the mechanism by which a cell identifies and corrects double strand breaks in its DNA by using homologous sequences elsewhere in the genome to prime repair synthesis. Without wishing to be bound by theory, it is believed that there are two types of HDR: gene conversion, and single-strand annealing. In gene conversion, an identical sequence, e.g. sister chromatid, is used as template to copy and replace damaged DNA. Single stranded 3' overhands are generated at the DSB by a complex comprising MRE11, RAD50, and NBS1 ("MRN complex"). This single strand DNA is then bound by BRCA2, which recruits RAD51. RAD51 catalyzes the search for homologous target sequence, invades the sequence at the site of homology, and initiates DNA synthesis using the homologous sequence as template. In single strand annealing, homologous sequences on either side of the DSB are aligned and annealed by the action of RAD52, followed by the deletion of the intermediate noncomplementary sequence. HDR is the major route of repair in the S and $G_2$ phases of the cell cycle. An agent that promotes HDR is an agent that promotes the activity of the aforementioned pathway, e.g. by promoting the activity of the aforementioned proteins, as will be discussed in greater detail below and as is understood in the art.

By "apoptosis", it is meant the process of programmed cell death (PCD) that may occur in a cell. Apoptosis is characterized by cell blebbing, loss of cell membrane asymmetry and attachment, cell shrinkage, nuclear fragmentation, chromatin condensation, and chromosomal DNA fragmentation. By "DNA-PKcs-directed apoptosis" it is meant apoptosis that is induced, promoted, or enhanced by DNA-PKcs activity.

By the "pro-apoptotic activity" of an agent, it is meant an activity that promotes apoptosis. The pro-apoptotic activity of an agent can be determined by assessing the extent of apoptosis or of viability in a cell population following the addition (e.g. gain of function, e.g. by overexpression) and/or removal (e.g., loss of function, e.g. by knockout) of that agent as known in the art and discussed in greater detail below.

By "DNA-PKcs" it is meant the catalytic subunit (cs) of the DNA-dependent serine/threonine protein kinase (DNA-PK). DNA-PKcs activity promotes the NHEJ mechanism of DSBR to repair DNA following damage, transposition, and V(D)J recombination. DNA-PKcs activity has also been found to promote apoptosis. DNA-PKcs protein is encoded by the PRKDC gene; the nucleotide sequence of the gene and the amino acid sequence of the protein encoded by it may be found at Genbank Accession Nos. NM_006904.6 (isoform 1) and NM_001081640.1 (isoform 2).

By "Ku" or "Ku70/Ku80" it is meant the heterodimeric complex that interacts with DNA-PKcs to form DNA-PK. Ku interaction with DNA-PKcs promotes DSBR. Ku consists of two subunits, Ku70 and Ku80, with molecular masses of approximately 70 and 80 kDa, respectively. Ku70 is encoded by the XRCC6 gene (also known as G22P1); the nucleotide sequence of the gene and the amino acid sequence of the protein encoded by it may be found at Genbank Accession No. NM_001469.3. Ku80 is encoded by the XRCC5 gene; the nucleotide sequence of the gene and the amino acid sequence of the protein encoded by it may be found at Genbank Accession No. NM_021141.3.

By the "c-Jun N-terminal kinase family" or "JNK family" it is meant the family of protein kinases that are members of the mitogen activated protein kinase (MAP kinase, or MAPK) family. The activation of JNK family members induces apoptosis. JNK family members include JNK/JNK1/MAPK8, JNK2/MAPK9, and JNK3/MAPK3. JNK/JNK1/MAPK8 and JNK2/MAPK9 are ubiquitously expressed. JNK3/MAPK10 is expressed more strongly in brain, heart and testis than in other tissues. The amino acid sequence for JNK1 and the nucleotide sequence that encodes it may be found at Genbank Accession Nos. NM_002750.2 (isoform alpha 1), NM_139049.1 (isoform alpha 2), NM_139046.1 (isoform beta 1), and NM_139047.1 (isoform beta 2). The amino acid sequence for JNK2 and the nucleotide sequence that encodes it may be found at Genbank Accession Nos. NM_139068.2 (isoform alpha 1), NM_002752.4 (isoform alpha 2), NM_139069.2 (isoform beta 1), NM_139070.2 (isoform beta 2), and NM_001135044.1 (isoform gamma). The amino acid sequence for JNK3 and the nucleotide sequence that encodes it may be found at Genbank Accession Nos. NM_002753.3 (isoform 1), NM_138982.2 (isoform 2), NM_138980.2 (isoform 3), NM_138981.2 (isoform 4).

By "BIM", "bcl-2 interacting mediator of cell death", or "BCL2L11" it is meant the Bcl3-homology domain 3 (BH3)-containing protein. BIM is an apoptosis activator. The amino acid sequence for BIM and the nucleic acid sequence that encodes it may be found at Genbank Accession Nos. NM_138621.3 (isoform 1), NM_006538.3 (isoform 6), and NM_207002.2 (isoform 9).

By "BIF", "BIF-1", "Bax-interacting factor 1", "endophilin-1", or "SH3GLB1" it is meant the Src-homology domain 3 (SH3)-containing protein that interacts with Bax protein. BIF is an apoptosis activator. The amino acid sequence for BIF and the nucleic acid sequence that encodes it may be found at Genbank Accession No. NM_016009.3.

By "effective amount" or "therapeutically effective amount" it is meant a dosage sufficient to provide for a change in the disease state being treated or to otherwise provide the desired effect (e.g., a reduction in the number of cells undergoing apoptosis, an increase in the viability of a cell population, an increase in the amount of double strand break repair occurring, a reduction in the number of double strand breaks, etc.). The precise dosage will vary according to a variety of factors such as subject-dependent variables (e.g., weight, age, etc.), the disease, and the treatment being effected. For example, by "an effective amount of an agent that promotes DSBR", it is meant an amount of agent that is effective in promoting DSBR by about 1.5 fold or more, i.e. 1.5-fold, 2-fold, 3-fold, 4-fold, 5-fold, 7-fold, 10-fold, 15-fold, or 20-fold or more. By "an effective amount of an agent that inhibits DNA-PKcs-directed apoptosis", it is meant an amount of agent that is effective in inhibiting apoptosis induced or mediated by DNA-PKcs by about 1.5 fold or more, i.e. 1.5-fold, 2-fold, 3-fold, 4-fold, 5-fold, 7-fold, 10-fold, 15-fold, or 20-fold or more.

By a "naïve lymphocyte" it is meant a lymphocyte that has reached a developmental state wherein it is ready to be exposed to antigen, e.g. a naïve T lymphocyte, or a naïve B cell, e.g. a mature B cell.

By "naïve T lymphocyte" or "unprimed T lymphocyte" it is meant a T cell that immature, i.e. has successfully undergone positive and negative selection in the thymus, but (unlike activated T cells or memory T cells) has not yet encountered cognate antigen in the periphery. Naïve T lymphocytes are commonly characterized by the surface expression of L-selectin (CD62L) and CD45RA; the absence of the activation markers CD25, CD44 or CD69; and the absence of $T_{H1}$, $T_{H2}$, $T_{reg}$, or memory T cell markers, such as the edited CD45 isoforms, e.g. CD45RO. Naïve T cells are quiescent and non-dividing, and require the common-gamma chain cytokines IL-7 and IL-15 for homeostatic survival. Recognition by a naive T cell clone of its cognate antigen results in the initiation of an acquired immune response. In the ensuing response, the T cell acquires an "activated" phenotype ($CD25^+$, $CD44^+$, $CD62L^{low}$, $CD69^+$), and may further differentiate into a memory T cell.

By a "naïve B lymphocyte", "naïve B cell", "unprimed B lymphocyte", or "unprimed B cell" it is meant a B cell that has not yet encountered cognate antigen. A naïve B cell may be an immature B cell or a mature B cell; in other words, it has undergone VDJ recombination of both heavy and light chains, but (unlike activated B cells) has not yet encountered cognate antigen. Naïve B cells are commonly characterized by the surface expression of CD19, CD20, B220, as well as IgM (immature B cell) or IgM and IgD (mature B cell); and the absence of plasma cell or memory cell markers as are well known in the art.

By a "hematopoietic stem cell" or "HSC" it is meant a cell that can a) self-renew and b) differentiate to produce all mature blood cell types. Hematopoietic stem cells are identifiable in humans by the following combination of markers, without limitation: $Lin^-CD34^+CD38^-CD90^+CD45RA^-$.

By a "hematopoietic progenitor cell" it is meant a descendent of a hematopoietic stem cell that may give rise to a subpopulation of cells of the hematopoietic lineage. For example, the earliest known lymphoid-restricted cell in adult mouse bone marrow is the common lymphocyte progenitor (CLP), and the earliest known myeloid-restricted cell is the common myeloid progenitor (CMP). A complete description of these cell subsets may be found in Akashi et al. (2000) Nature 404(6774):193, U.S. Pat. No. 6,465,247; and published application U.S. Ser. No. 09/956,279 (common myeloid progenitor); Kondo et al. (1997) Cell 91(5):661-7, and International application WO99/10478 (common lymphoid progenitor); and is reviewed by Kondo et al. (2003) Annu Rev Immunol. 21:759-806, each of which is herein specifically incorporated by reference.

By "surface expression" of a particular protein marker, it will be understood by those of skill in the art that the stated expression levels reflect detectable amounts of the marker protein on the cell surface. A cell that is negative for staining (the level of binding of a marker specific reagent is not detectably different from an isotype matched control) may still express minor amounts of the marker. And while it is commonplace in the art to refer to cells as "positive" or "negative" for a particular marker, actual expression levels are a quantitative trait. The number of molecules on the cell surface can vary by several logs, yet still be characterized as "positive". The staining intensity of cells can be monitored by flow cytometry, where lasers detect the quantitative levels of fluorochrome (which is proportional to the amount of cell surface marker bound by specific reagents, e.g. antibodies). Although the absolute level of staining may differ with a particular fluorochrome and reagent preparation, the data can be normalized to a control. In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. "Low" positively stained cells have a level of staining that is above the brightness of an isotype matched control, but is not as intense as the most brightly staining cells normally found in the population. An alternative control may utilize a substrate having a defined density of marker on its surface, for example a fabricated bead or cell line, which provides the positive control for intensity. Flow cytometry-based techniques can be employed with marker-specific antibodies to confirm the presence of the subject naïve lymphocytes in a cell population. Other techniques may also be employed, e.g. immunohistochemistry, western blotting, etc.

The terms "individual," "subject," "host," and "patient," are used interchangeably herein and refer to any mammalian subject for whom diagnosis, treatment, or therapy is desired, particularly humans.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

DESCRIPTION

As summarized above, aspects of the invention include methods for improving immune system function in individuals. By "immune system function" it is meant the ability of an individual's immune system to protect the body, for example, to fight infection, to develop and recover from inflammation, to respond to vaccines, and to identify and remove tumorigenic cells. By "improved immune system function", it is meant that the frequency and extent of infection is decreased, the duration of inflammation is reduced, response to vaccines is improved, and the rate of developing cancer is decreased by e.g. 2-fold or more, 5-fold or more, or 10-fold or more, as compared to these immune responses in the individual prior to treatment with the method.

Methods of the invention find particular use in improving immune system function in individuals that have a condition in which lymphocytes have elevated amounts of DNA double strand breaks (DSB) relative to a normal control. By a "normal control" it is meant an unaffected individual, e.g. an individual that is unaffected by the condition; or, when the individual that has an elevated number of DSBs due to older age, a healthy individual under the age of 40. Following the methods of the invention, the number of DSBs in hematopoietic progenitor cells and naïve lymphocytes is reduced, the viability of hematopoietic progenitor cells and naïve lymphocytes is increased, the diversity of lymphocytes is increased, the migration of lymphocytes, i.e. chemotaxis, rolling and extravasation of lymphocytes into tissues, is improved, antibody production is improved, and/or cytotoxic lymphocyte response is improved.

In performing methods of the invention, naïve lymphocytes are contacted with an effective amount of an agent that inhibits DNA-PKcs-directed apoptosis or an effective amount of an agent that promotes double strand break repair (DSBR). In some embodiments, lymphocytes are contacted with both an effective amount of an agent that inhibits DNA-PKcs-directed apoptosis and an effective amount of an agent that promotes double strand break repair (DSBR). As discussed above, DSBR occurs by one of two mechanisms in the cell: non-homologous end joining (NHEJ), and homology-directed repair (HDR). Agents that promote either of these mechanisms find use in the present application.

Subject agents, i.e. agents that inhibit DNA-PKcs-directed apoptosis and agents that promote DSBR, that find use in the present invention include nucleic acids, for example, nucleic acids that encode siRNA, shRNA or antisense molecules, e.g. DNA-PKcs-specific siRNA, or nucleic acids that encode polypeptides, e.g. nucleic acids that encode for Ku70/Ku80 or other polypeptides if the NHEJ or HDR pathways. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the pluripotent cells are contacted with vectors comprising the nucleic acid of interest such that the vectors are taken up by the cells. Methods for contacting cells with nucleic acid vectors, such as electroporation, calcium chloride transfection, and lipofection, are well known in the art.

Alternatively, the nucleic acid of interest may be provided to the subject cells via a virus. In other words, the pluripotent cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject CD33+ differentiated somatic cells are targeted by the packaged viral particles. Methods of introducing the retroviral vectors comprising the nucleic acid encoding the reprogramming factors into packaging cell lines and of collecting the viral particles that are generated by the packaging lines are well known in the art.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-β-actin promoter, or cell- or tissue specific promoter, such as promoters that are active in particular cell populations, or inducible promoters, such as promoters that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing agents to the subject cells may include genes that must later be removed, e.g. using a recombinase system such as Cre/Lox, or the cells that express them destroyed, e.g. by including genes that allow selective toxicity such as herpesvirus TK, bcl-xs, etc Subject agents that find use in the present invention also include polypeptides, e.g. Ku70/Ku80 polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

If the polypeptide agent is to modulating signaling intracellularly, the polypeptide may comprise the polypeptide sequences of interest fused to a polypeptide permeant domain. A number of permeant domains are known in the art and may be used in the non-integrating polypeptides of the present invention, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO:13). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

If the polypeptide agent is to modulating signaling extracellularly, the polypeptide may be formulated for improved stability. For example, the peptides may be PEGylated, where the polyethyleneoxy group provides for enhanced lifetime in the blood stream. The SHBG polypeptide may be fused to another polypeptide to provide for added functionality, e.g. to increase the in vivo stability. Generally such fusion partners are a stable plasma protein, which may, for example, extend the in vivo plasma half-life of the SHBG polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the SHBG polypeptide also will be produced and employed as a multimer having substantially the same structure as the stable plasma protein precursor. These multimers will be homogeneous with respect to the polypeptide agent they comprise, or they may contain more than one polypeptide agent.

Stable plasma proteins are proteins which typically exhibit in their native environment an extended half-life in the circulation, i.e. greater than about 20 hours. Examples of suitable stable plasma proteins are immunoglobulins, albumin, lipoproteins, apolipoproteins and transferrin. The polypeptide agent typically is fused to the plasma protein, e.g. IgG at the N-terminus of the plasma protein or fragment thereof which is capable of conferring an extended half-life upon the SHBG polypeptide. Increases of greater than about 100% on the plasma half-life of the SHBG polypeptide are satisfactory. Ordinarily, the SHBG polypeptide is fused C-terminally to the N-terminus of the constant region of immunoglobulins in place of the variable region(s) thereof, however N-terminal fusions may also find use. Typically, such fusions retain at least functionally active hinge, CH2 and CH3 domains of the constant region of an immunoglobulin heavy chain, which heavy chains may include IgG1, IgG2a, IgG2b, IgG3, IgG4, IgA, IgM, IgE, and IgD, usually one or a combination of proteins in the IgG class. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, the polypeptides may be synthesized according to known methods.

The site at which the fusion is made may be selected in order to optimize the biological activity, secretion or binding characteristics of the SHBG polypeptide. The optimal site will be determined by routine experimentation.

In some embodiments the hybrid immunoglobulins are assembled as monomers, or hetero- or homo-multimers, and particularly as dimers or tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of basic four-chain units held together by disulfide bonds. IgA immunoglobulin, and occasionally IgG immunoglobulin, may also exist in a multimeric form in serum. In the case of multimers, each four chain unit may be the same or different.

The polypeptide agent for use in the subject methods may be produced from eukaryotic produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention as subject agents are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Subject agents that find use in the present invention also include small molecules, e.g. small molecule inhibitors of DNA-PKcs, small molecule inhibitors of proteins that activate DNA-PKcs, etc. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992). Small molecule compounds can be provided directly to the medium in which the cells are being cultured, for example as a solution in DMSO or other solvent.

As discussed above in some embodiments, a subject agent that finds use in the present invention is an agent that inhibits DNA-PKcs-directed apoptosis. Examples of agents that inhibit DNA-PKcs-directed apoptosis include those that inhibit JNK activity, e.g. small molecule compounds that inhibit JNK activity such as JNK inhibitor II (also known as SP600125, anthra(1,9-cd)pyrazol-6(2H)-one, or 1,9-pyrazoloanthrone), 2H-Dibenzo(cd,g) indazol-6-one, 3-(4-fluoro-phenyl)-5-(2H-(1,2,4) triazol-3-yl)-1H-indazole, 3-(4-(2-Piperidin-1-yl-ethoxy)-cyclohexa-1,5-dienyl)-5-(2H-(1,2,4)triazol-3-yl)-1H-indazole, XG-102 (also known as D-JNKI-1) and the like; JNK1, JNK2, and/or JNK3-specific siRNA, shRNA or antisense RNA; or an antibody or a fragment thereof that immunospecifically binds to JNK or another component of the JNK pathway thus inhibiting JNK activity. Examples of agents that inhibit DNA-PKcs-directed apoptosis also include those that inhibit BIM activity, e.g. BIM-specific siRNA, shRNA, or anti-sense RNA. Examples of agents that inhibit DNA-PKcs-directed apoptosis also include those that inhibit BIF-1 activity, e.g. BIF-1-specific siRNA, shRNA, or anti-sense RNA. Example of agents that inhibit DNA-PKcs-directed apoptosis also include those that inhibit DNA-PKcs activity, e.g. small molecule inhibitors of DNA-PKcs, e.g. 1-(2-hydroxy-4-morpholin-4-ylphenyl) ethanone (IC86621, Sigma Aldrich), 2-(morpholin-4-yl)-benzo[h]chomen-4-one) (NU7026, Tocris Bioscience), 8-(4-Dibenzothienyl)-2-(4-morpholinyl)-4H-1-benzopyran-4-one (NU7441), IC486241 (ICC), vanillin, and the like; DNA-PKcs-specific siRNA, shRNA, or anti-sense RNA; or an antibody or a fragment thereof that immunospecifically binds to DNA-PKcs thus inhibiting DNA-PKcs activity.

The agent that inhibits DNA-PKcs-directed apoptosis is provided in an effective amount to inhibit DNA-PKcs-directed apoptosis. An effective amount is the amount of agent to reduce, suppress, or inhibit apoptosis in cells with elevated amounts of DSBs by about 1.5 fold or more, e.g. 1.5-fold, 2-fold, 3-fold, 4-fold, 5-fold, 7-fold, 10-fold, 15-fold, or 20-fold. In other words, it is the amount required to promote an increase in viability of a subject cell population by about 1.5 fold or more, e.g. 1.5-fold, 1.75-fold, 2-fold, 3-fold, 4-fold, 5-fold, 6-fold, 7-fold, 8-fold, 10-fold, 15-fold, or 20-fold or more relative to the viability observed in the absence of agent. Said differently, it is the amount of agent that is effective in increasing the number of subject cells by about 50%, 75%, 100%, 150%, 200%, 300%, 400%, 500%, 600%, 700%, 1000% or more. In some instances, elevated numbers of DSBs will still be observed. In other instances, e.g. 2 hours, 4 hours, 6 hours 8 hours, 10 hours, 12 hours, 18 hours, 24 hours, 36 hours, 48 hours, or 72 hours after contact with the subject agent, the number of DSBs will be at levels normal to control levels. Apoptosis and cell viability may be assessed by any methods known in the art for assessing apoptosis or viability, e.g. Terminal deoxynucleotidyl transferase dUTP nick end labeling (TUNEL), staining with Annexin V or 7-Aminoactinomycin D (7-AAD), analysis of propidium iodide uptake, flow cytometry following incubation of a cell sample with subject cell-specific antibodies, etc.

In some embodiments, a subject agent that finds use in the present invention is an agent that promotes double strand break repair (DSBR). Examples of agents that promote DSBR include agents that promote the non-homologous end joining (NHEJ), e.g. an agent that promotes the activity of Ku70, Ku80, XRCC4, DNA ligase IV, or XLF, e.g. a Ku70, Ku80, XRCC4, DNA ligase IV, or XLF polypeptide or active fragment thereof, or a nucleic acid encoding a Ku70, Ku80, XRCC4, DNA ligase IV, or XLF polypeptide or active fragment thereof, as is known in the art. Other examples of agents that promote DSBR include agents that promote homology-directed repair (HDR), e.g. an agent that promotes MRE11, RAD50, NBS1, RAD51, RAD52, BRCA1 or BRCA2, e.g. a MRE11, RAD50, NBS1, RAD51, RAD52, BRCA1 or BRCA2 polypeptide or active fragment thereof, or a nucleic acid encoding a MRE11, RAD50, NBS1, RAD51, RAD52, BRCA1 or BRCA2 polypeptide or active fragment thereof, as is known in the art.

The agent(s) that promotes double strand break repair (DSBR) is provided in an effective amount. That is, the subject agents are provided in an amount that is effective in activating, promoting, or enhancing DSBR by about 1.5 fold or more, e.g. 1.5-fold, 2-fold, 3-fold, 4-fold, 5-fold, 7-fold, 10-fold, 15-fold, or 20-fold or more. In other words, the subject agents will reduce the number of DSBs in the subject cells by about 50%, 75%, 100%, 150%, 200%, 300%, 400%, 500%, 600%, 700%, 1000% or more, typically within about 2 hours, 4 hours, 6 hours 8 hours, 10 hours, 12 hours, 18 hours, 24 hours, 36 hours, 48 hours, or 72 hours of contact with the subject agent. The effective amount of an agent to activate/promote/enhance DSBR may be readily determined by one of ordinary skill in the art by, for example, contacting any cell comprising DSBs (e.g. naïve T lymphocytes from Rheumatoid Arthritis patients; B lymphocytes undergoing VDJ recombination; any cells treated with $H_2O_2$, e.g. 50-250 μM $H_2O_2$ diluted in culture medium, e.g. DMEM, for about 1 hour; and the like) with the subject agent and measuring (e.g. by Comet Assay (R&D Systems); by staining for 53BP1 with anti-53BP1 antibody, etc.) the amount of DSBs after contact relative to a control population not contacted with the subject agent.

As mentioned above, in some embodiments, the agent that is provided is an agent that inhibits DNA-PKcs-directed apoptosis. In some embodiments, the agent that is provided is an agent that promotes double strand break repair. In some embodiments, an agent that inhibits DNA-PKcs-directed apoptosis and the agent that promotes double strand break repair are provided. In some such embodiments, the agent that inhibits DNA-PKcs-directed apoptosis may be provided first, and the agent that promotes double strand break repair provided second; or vice versa. In other such embodiments, the agent that inhibits DNA-PKcs-directed apoptosis and the agent that promotes double strand break repair are provided at the same time.

In methods of the invention, naïve lymphocytes are contacted with the one or more of the subject agents. In some embodiments, the naive lymphocytes are naïve T lymphocytes ("naïve T cells"), e.g. CD4+ or CD8+ T cells. Naïve CD4+ or CD8+ T cells are identifiable as such by the expression of CD4 or CD8, respectively, on their cell surface in addition to the aforementioned markers characteristic of naïve T lymphocytes ($CD62L^+$, $CD25^-$, $CD44^-$, $CD69^-$, $CD45RA^+$, $CD45RO^-$). In some embodiments, the naïve lymphocytes are naïve B cells, i.e. mature B cells. In some embodiments, the naïve lymphocytes are hematopoietic progenitor cells.

In some embodiments, the lymphocytes are contacted with the subject agent(s) ex vivo. In other words, lymphocytes are removed from the individual and contacted with the subject agent in vitro, then returned to the individual. The lymphocytes may be from a neonate, a juvenile or an adult, and from any tissue or body fluid known in the art to comprise naïve lymphocytes. Any sampling method that retrieves naïve lymphocytes may be used, e.g. a peripheral blood sample, a bone marrow sample, etc. For example, lymphocytes may be harvested by automated blood collection, or "apheresis," i.e. leukocytapheresis. In apheresis, a blood sample is passed through a machine that separates out certain components, e.g. platelets, erythrocytes, plasma, or leukocytes, and returns the remaining blood components to the blood stream. In leukocytapheresis, leukocytes, including lymphocytes, are selectively removed. Blood components acquired by apheresis are routinely used as a component of various therapies. For example, apheresis is commonly used for harvesting HSCs for autologous transplantation. Equipment for apheresis allows for the collection of several billion leukocytes for one session. As another example, a whole blood sample may be collected and fractionated by density gradient centrifugations, and the buffy coat (comprising the leukocytes) isolated for use. In some such instances, the leukocytes are obtained from fresh blood, e.g. a whole blood sample freshly drawn from a patient, or drawn from a patient and stored refrigerated. In other such instances, the leukocytes are obtained from frozen blood, e.g. a whole blood sample that is obtained and frozen, e.g. 1 week or more, e.g. 1 month or more, e.g. 1 year or more, e.g. up to 10 years. If necessary, multiple harvests may be performed to obtain the required amount of lymphocytes.

In some embodiments, the lymphocytes are contacted as part of a heterogeneous population of cells, e.g. a heterogeneous population of blood cells. For example, the whole sample or a heterogeneous fraction thereof is contacted with agent. In other embodiments, the sample is enriched for lymphocytes, and the enriched population of cells is contacted with agent. By an "enriched population of cells" it is meant a population of cells that is substantially comprised of a particular cell of interest. In an enriched population, 50% or more of the cells in the population are the cells of interest, e.g. 50%, 60%, 70%, usually 80%, 85%, 90%, more usually 92%, 95%, or 98%, sometimes as much as 100% of the cells in the population. The separation of cells of interest from a complex mixture or heterogeneous culture of cells may be performed by any convenient means known in the art, for example, by affinity separation techniques such as magnetic separation using magnetic beads coated with an affinity reagent, affinity chromatography, or "panning" with an affinity reagent attached to a solid matrix, e.g. plate, or other convenient technique. Other techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the desired cells. The affinity reagents may be antibodies that are specific for the lymphocytes of interest. Alternatively, specific receptors or ligands for markers of the lymphocytes of interest may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art. The affinity reagents are added to a suspension of cells, and incubated for a period of time sufficient to bind the available cell surface antigens. The incubation will usually be at least about 5 minutes and usually less than about 60 minutes. It is desirable to have a sufficient concentration of affinity reagent in the reaction mixture, such that the efficiency of the separation is not limited by lack of reagent. The appropriate concentration is determined by titration. The medium in which the cells are separated will be any medium that maintains the viability of the cells. A preferred medium is phosphate buffered saline containing from 0.1 to 0.5% BSA or 1-4% goat serum. Various media are commercially available and may be used according to the nature of the cells, including Dulbecco's Modified Eagle Medium (DMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, goat serum etc. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

In embodiments in which the naïve lymphocytes are contacted by subject agent(s) ex vivo, the lymphocytes are typically contacted under conditions that promote their survival, for example, culturing at about 37° C. in nutrient media such as DMEM, Iscove's modified DMEM, or RPMI 1640, supplemented with goat serum, fetal calf serum, or horse serum (about 5-10%), L-glutamine, a thiol, particularly 2-mercaptoethanol, antibiotics, and e.g. penicillin and streptomycin. Culture medium may be liquid or semi-solid, e.g. containing agar, methylcellulose, etc. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors, e.g. IL-2, IL-7, IL-15, etc; see, e.g. Ma et al. (2006) Ann Rev. Immunology 24:657-679, and Surh et al. (2008) Immunity 29(6):848-862, the complete disclosures of which are incorporated herein by reference.

Naïve lymphocytes may be contacted with the subject agent(s) ex vivo by any of a number of well-known methods in the art. For example, polypeptides (including antibodies) or small molecule agents may be provided to the cells in the media in which the cells are being cultured. Nucleic acids agents may be provided to the cells on vectors under conditions that are well known in the art for promoting their uptake, for example electroporation, calcium chloride transfection, and lipofection. Alternatively, nucleic acids encoding the agent may be provided to the cells via a virus, i.e. the cells are contacted with viral particles comprising the nucleic acid agent. Retroviruses, for example, lentiviruses, are particularly suitable to the method of the invention, as they can be used to transfect non-dividing cells (see, for example, Uchida et al. (1998) P.N.A.S. 95(20):11939-44). Commonly used retroviral vectors are "defective", i.e. unable to produce viral proteins required for productive infection. Rather, replication of the vector requires growth in a packaging cell line.

In some embodiments, naïve lymphocytes are contact with the subject agent(s) in vivo. The present invention provides pharmaceutical compositions comprising one or more agents that promotes DSBR, and/or that inhibits DNA-PKcs-directed apoptosis. A subject agent, i.e. an agent that promotes DSBR, or agent that inhibits DNA-PKcs-directed apoptosis, that is a component of a pharmaceutical composition is also referred to herein as an "active agent." The subject active agent is formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) N. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The term "unit dosage form," as used herein, refers to physically discrete units suitable as unitary dosages for human and animal subjects, each unit containing a predetermined quantity of a subject active agent calculated in an amount sufficient to produce the desired effect in association with a pharmaceutically acceptable diluent, carrier or vehicle. The specifications for a subject active agent depend on the particular compound employed and the effect to be achieved, and the pharmacodynamics associated with each compound in the host.

In the subject methods, a subject active agent may be administered to the host using any convenient means capable of resulting in the desired outcome, e.g., reduction of disease, reduction of a symptom of a disease, etc. Thus, a subject modulator of DNP-PKcs activity can be incorporated into a variety of formulations for therapeutic administration. More particularly, a subject modulator of DNP-PKcs activity can be formulated into pharmaceutical compositions by combination with appropriate, pharmaceutically acceptable carriers or diluents, and may be formulated into preparations in solid, semi solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

In pharmaceutical dosage forms, the subject agent(s) ("active agent(s)") may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, a subject active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject active agent can be utilized in aerosol formulation to be administered via inhalation. A subject active agent can be formulated into pressurized acceptable propellants such as dichlorodifluoromethane, propane, nitrogen and the like.

Furthermore, a subject active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject active agent. Similarly, unit dosage forms for injection or intravenous administration may comprise a subject active agent in a composition as a solution in sterile water, normal saline or another pharmaceutically acceptable carrier.

A subject active agent can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

A pharmaceutical preparation comprising a subject active agent can further include one or more non-toxic auxiliary substances such as antibacterial components which are non-injurious in use, for example, thimerosal, benzalkonium chloride, methyl and propyl paraben, benzyldodecinium bromide, benzyl alcohol, chlorhexidine, or phenylethanol; buffering ingredients such as sodium borate, sodium acetate, sodium citrate, or gluconate buffers; and other conventional ingredients such as sodium chloride, sorbitan monolaurate, triethanolamine, polyoxyethylene sorbitan monopalmitate, ethylenediaminetetraacetic acid, and the like.

Topical Formulations.

A subject active agent can be formulated for topical administration to the skin. For example, a subject active agent can be formulated with one or more dermatologically acceptable excipients.

The term "dermatologically acceptable," as used herein, means that the compositions or components thereof so described are suitable for use in contact with human skin without undue toxicity, incompatibility, instability, allergic response, and the like.

Suitable excipients include emollients; humectants; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and the like.

A variety of emollients may be employed to yield the conditioning component of the present invention. These emollients may be selected from one or more of the following classes: triglyceride esters that include, but are not limited to, vegetable and animal fats and oils such as castor oil, cocoa butter, safflower oil, cottonseed oil, corn oil, olive oil, cod liver oil, almond oil, avocado oil, palm oil, sesame oil, squalene, kikui oil and soybean oil; acetoglyceride esters, such as acetylated monoglycerides; alkyl esters of fatty acids having 10 to 20 carbon atoms which include, but are not limited to, methyl, isopropyl, and butyl esters of fatty acids such as hexyl laurate, isohexyl laurate, isohexyl palmitate, isopropyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; wax esters such as beeswax, spermaceti, myristyl myristate, stearyl stearate; forming a mixture of ether esters; and vegetable waxes including, but not limited to, carnauba and candelilla waxes; and cholesterol fatty acid esters.

Humectants of the polyhydric alcohol-type are suitable for use. Typical polyhydric alcohols include polyalkylene glycols and more preferably alkylene polyols and their derivatives, including propylene glycol, dipropylene glycol, tripropylene glycol, polyethylene glycol and derivatives thereof, sorbitol, hydroxypropyl sorbitol, erythritol, threitol, pentaerythritol, xylitol, glucitol, mannitol, hexylene glycol, 1,3-butylene glycol, 1,2,6-hexanetriol, glycerol, ethoxylated glycerol, propoxylated glycerol, sodium 2-pyrrolidone-5-carboxylate, soluble collagen, gelatin and mixtures thereof.

Also useful herein are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and mixtures thereof.

A composition comprising a subject active agent can include a dermatologically-acceptable hydrophilic diluent. Non-limiting examples of hydrophilic diluents are water, organic hydrophilic diluents such as lower monovalent alcohols (e.g., C1-C4 alcohols) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. A composition comprising a subject active agent can contain from about 60% to about 99.99% of a hydrophilic diluent.

A composition comprising a subject active agent can include a dermatologically acceptable carrier. An example of a suitable carrier is an emulsion comprising a hydrophilic phase comprising a hydrophilic component, e.g., water or other hydrophilic diluent, and a hydrophobic phase comprising a hydrophobic component, e.g., a lipid, oil or oily material. The hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions can comprise from about 1% to about 50% of the dispersed hydrophobic phase and from about 1% to about 98% of the continuous hydrophilic phase; water-in-oil emulsions can comprise from about 1% to about 98% of the dispersed hydrophilic phase and from about 1% to about 50% of the continuous hydrophobic phase.

A subject active agent can be formulated with common excipients, diluents, or carriers, and formed into lotions, creams, solutions, suspensions, powders, aerosols, emulsions, salves, ointments and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinylpyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. A composition comprising a subject active agent can include thickening agents such as cellulose and/or cellulose derivatives. A composition comprising a subject modulator of DNP-PKcs activity can include contain gums such as xanthan, guar or carbo gum or gum arabic, or alternatively poly(ethylene glycol)s, bentones and montmorillonites, and the like.

A composition comprising a subject active agent can further include one or more additional agents such as, for example, antioxidants, surfactants, preservatives, film-forming, keratolytic or comedolytic agents, perfumes, flavorings, and colorings. Antioxidants such as t-butylhydroquinone, butylated hydroxyanisole, butylated hydroxytoluene and α-tocopherol and its derivatives can be added.

Furthermore, composition comprising a subject active agent can further include one or more additional therapeutic agents, for example, anti-microbial agents, pain relievers, anti-inflammatory agents, and the like, depending, e.g., on the condition being treated.

Continuous Delivery.

In some embodiments, a subject active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, nonexchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, the subject active agent is delivered using an implantable drug delivery system, e.g., a system that is programmable to provide for administration of a subject active agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Oral Formulations.

In some embodiments, a subject active agent is formulated for oral delivery to an individual in need of such an agent.

For oral delivery, a subject formulation comprising a subject active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, a subject active agent is formulated with one or more pharmaceutical excipients and coated with an enteric coating, as described in U.S. Pat. No. 6,346,269. For example, a solution comprising a subject active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for a subject active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include a subject active agent formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) Biomaterials 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include a subject active agent with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Inhalational Formulations.

A subject active agent will in some embodiments be administered to a patient by means of a pharmaceutical delivery system for the inhalation route. A subject active agent can be formulated in a form suitable for administration by inhalation. The inhalational route of administration provides the advantage that the inhaled drug can bypass the blood-brain barrier. The pharmaceutical delivery system is one that is suitable for respiratory therapy by delivery of a subject active agent to mucosal linings of the bronchi. This invention can utilize a system that depends on the power of a compressed gas to expel the subject active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains a subject active agent, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

A subject active agent can also be formulated for delivery with a nebulizer, which is an instrument that generates very fine liquid particles of substantially uniform size in a gas. For example, a liquid containing the subject active agent is dispersed as droplets. The small droplets can be carried by a current of air through an outlet tube of the nebulizer. The resulting mist penetrates into the respiratory tract of the patient.

A powder composition containing a subject active agent, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present invention. A subject active agent can be formulated in basically three different types of formulations for inhalation. First, a subject modulator of DNA-PKcs activity can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, a subject active agent can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

A subject active agent can be formulated into dry powder formulations. Such formulations can be administered by simply inhaling the dry powder formulation after creating an aerosol mist of the powder. Technology for carrying such out is described within U.S. Pat. No. 5,775,320 and U.S. Pat. No. 5,740,794.

A subject active agent can be formulated for targeted delivery to a cell or tissue of interest, e.g. CD4+ T lymphocytes, or targeted expression by a cell or tissue of interest, e.g. CD4+ T lymphocytes. Targeted delivery and/or targeted expression may be achieved by any convenient method suitable to the type of agent as known in the art. For example, small molecule inhibitor agents and peptide agents may be targeted to cells of interest by crosslinking the agent to an antibody that is specific for an antigen expressed by the cell of interest, e.g. a CD4-specific antibody. Targeted expression of nucleic acid agents may be achieved by operably linking the nucleic acid to a cell-specific promoter, e.g. the CD4-promoter, or to a conditionally active promoter, e.g. a drug-responsive promoter, e.g. a promoter that is responsive to tetracycline.

Dosages and Dosing.

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

For example, a subject active agent can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

An exemplary dosage may be a solution suitable for intravenous administration; a tablet taken from two to six times daily, or one time release capsule or tablet taken once a day and containing a proportionally higher content of active ingredient, etc. The time release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is in some embodiments one which provides up to about 1 μg to about 1,000 μg or about 10,000 μg of subject compound in a blood sample taken from the individual being treated, about 24 hours after administration of the compound to the individual.

Unit dosage forms for oral, vaginal or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound(s) in a composition as a solution in sterile water, normal saline or another pharmaceutically acceptable carrier.

In some embodiments, multiple doses of a subject active agent are administered. The frequency of administration of a subject active agent can vary depending on any of a variety of factors, e.g., severity of the symptoms, etc. For example, in some embodiments, a subject compound is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in some embodiments, a subject compound is administered continuously.

The duration of administration of a subject active agent, e.g., the period of time over which a subject active agent is administered, can vary, depending on any of a variety of factors, e.g., patient response, etc. For example, a subject compound can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, a subject compound is administered for the lifetime of the individual.

Routes of Administration.

A subject active agent is administered to an individual using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time of from about 2 weeks to about one month, from about one month to about 3 months, from about 3 months to about 6 months, from about 6 months to about 1 year, or longer than one year).

Conventional and pharmaceutically acceptable routes of administration include intranasal, intramuscular, intratracheal, subcutaneous, intradermal, transdermal, sublingual, topical application, intravenous, ocular, rectal, nasal, oral, and other enteral and parenteral routes of administration. Routes of administration may be combined, if desired, or adjusted depending upon the agent and/or the desired effect. The compound can be administered in a single dose or in multiple doses.

A subject active agent can be administered to a host using any available conventional methods and routes suitable for delivery of conventional drugs, including systemic or localized routes. In general, routes of administration contemplated by the invention include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, ocular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and vaginal or rectal (e.g., using a suppository) delivery.

Methods of administration of a subject active agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Following the methods of the invention, immune system function is improved in individuals with conditions characterized by immune systems that comprise naïve lymphocytes comprising elevated amounts of chromosomal DNA double strand breaks (DSB), i.e. aberrantly high numbers of DSBs relative to an unaffected individual, for example, an individual that is unaffected with the condition, or, in the case of an older individual, a healthy individual that is less than 40 years old. These improvements in immune system function may include an increase in the viability of hematopoietic progenitor cells and naïve lymphocytes, an increase in the diversity of lymphocytes, more efficient trafficking of lymphocytes, i.e. chemotaxis, rolling and extravasation of lymphocytes into tissues, an increase in antibody production and antibody specificity, and an improvement in cytotoxic lymphocyte response, which clinically results in a decrease in the frequency and extent of infections, a reduction in the extent of inflammation and a reduction in the amount of time it takes to resolve inflammation, an improved, i.e. faster and more robust, response to vaccines, and a decrease in the rate of developing cancer as compared to these immune responses in the individual before treatment with the method or in individuals with the same condition not treated with the method.

By "improved", it is meant a 2-fold increase or more in the described character, e.g. a 2-fold, 3-fold, 4-fold, 5-fold, 6-fold, 8-fold, 10-fold, 15-fold, or 20-fold or more increase in viability, diversity, trafficking, antibody production, and cytotoxic activity of lymphocytes, responsiveness to vaccines etc. By "a reduction" it is meant a 2-fold decrease or more in the described character, e.g. a 2-fold, 3-fold, 4-fold, 5-fold, 6-fold, 8-fold, 10-fold, 15-fold, or 20-fold reduction in the number of infections, the length of time to resolve infections, the number of inflammatory cells involved in inflammatory response, the length of time to resolve the inflammation response, and the probability of developing a cancer.

For example, an increase in the number of naïve lymphocytes is indicative of improved immune function. The number of naïve lymphocytes can be measured in any body fluid or tissue comprising lymphocytes, e.g. blood, lymph node, spleen, or bone marrow, e.g. by aspirating the fluid or taking a biopsy and counting the lymphocyte by any of a number of methods known in the art, e.g. by performing a complete blood count (CBC) test, performing flow cytometry with markers described above and as known in the art, etc. In some embodiments, the method comprises the step of measuring the number of naïve lymphocytes in an individual.

As another example, an increase in the diversity of naïve lymphocytes is indicative of improved immune function. By "diversity", it is meant the clonal representation of naïve lymphocytes, e.g. naïve T lymphocytes, in a blood sample, e.g. a sample of whole blood ranging from 50 to 500 ml. By an increase in diversity it is meant that the diversity of lymphocytes in an individual is increased relative to the diversity of lymphocytes observed in the individual prior to use of the methods, e.g. by 10-fold or more, 15-fold or more, 20-fold or more, 30-fold or more, or 40-fold or more, including 50-fold or more, 100-fold or more, such as 500-fold or more, 1000-fold or more, etc. relative to the diversity of lymphocytes observed in the individual prior to use of the methods. Lymphocyte may be measured by determining the number of a lymphocytes in an individual, for example by immunohistochemistry or flow cytometry of a blood sample or immune tissue, e.g. lymph node, spleen, etc., using any convenient markers specific for naïve T cells, e.g. as described further below. As a more stringent measurement, lymphocyte diversity may be measured by measuring the diversity of the B cell or T cell repertoire. For example, T cell diversity may be measured by measuring the diversity of the T cell receptor (TCR) repertoire, for example by flow cytometry, e.g., to detect the differences in Vβ family usage among various T-cell compartments; TCR clonotyping, which utilizes Vβ-Cβ or Vα-Caspecific PCR and denaturing gradient gel electrophoresis; immunoscoping, a PCR-based method that detects large expansions within Vβ families (see, e.g. Even, J A et al. Res Immunol 1995, 146:65-80); spectratyping or massive sequencing of T cell receptor repertoires (see, e.g., Zhou et al. Cancer Epidemiol. 2010 34(6):733-40; Mamedov et al. EMBO Mol. Med. 2011 3(4):201-7); isolating and characterizing a small subset of sequences and extrapolating their frequencies (based upon parameters such as Vβ frequency and possible αβ combinations) to the whole T cell pool; and AmpliCot analysis (see, e.g., Baum and McCune Nat. Methods 2006, 3(11): 895-901), in which the sequence diversity of PCT products are measured based upon DNA hybridization kinetics. In some embodiments, the method comprises the step of measuring the diversity of lymphocytes in an individual.

As another example, an increase in the functional activity of naïve lymphocytes is indicative of improved immune function, e.g. by measuring the levels of cytokines produced by lymphocytes, by measure the rate of migration or extent of trafficking of the lymphocytes, by measuring the cytotoxic activity of the lymphocytes, by measuring the proliferative capacity of the lymphocytes, etc. In some embodiments, the method comprises the step of measuring the functional activity of lymphocytes.

The above methods find use in improving immune function in conditions characterized by an immune systems that comprises naïve lymphocytes with elevated amounts of DNA double strand breaks (DSB) relative to a normal control, e.g. 1.5-fold more DSBs than lymphocytes from individuals unaffected by the condition, i.e. 1.5-fold, 2-fold, 2.5-fold, 3-fold, 4-fold, 5-fold, 6-fold, 7-fold, 8-fold, 10-fold, or more DSBs than the immune system of an unaffected individual. Such conditions include conditions in which the immune system has prematurely aged, for example, diseases that impose a chronic stress on the immune system and essentially create immune system exhaustion, e.g. Rheumatoid Arthritis, Psoriasis, demyelinating diseases (Multiple Sclerosis, Acute disseminated encephalomyelitis (ADEM)), Diabetes Mellitus (DM), etc.; conditions in which extensive replication pressure is applied, e.g. following a bone marrow transplant, wherein an entire immune system must be reconstituted from the transplanted cells; and age over 50 years, e.g. age 50 or more, age 55 or more, age 60 or more, age 65 or more, age 70 or more, age 75 or more, age 80, or more age 85 or more, i.e. after the thymus stops producing naïve T lymphocytes at about age 40.

As one non-limiting example, one condition that benefits from the pending claimed method is Rheumatoid Arthritis. Rheumatoid Arthritis is a chronic syndrome characterized by usually symmetric inflammation of the peripheral joints, potentially resulting in progressive destruction of articular and periarticular structures, with or without generalized manifestations. The cause is unknown. A genetic predisposition has been identified and, in Caucasian populations, localized to a pentapeptide in the HLA-DR beta1 locus of class II histocompatibility genes. Environmental factors may also play a role. Immunologic changes may be initiated by multiple factors. About 0.6% of all populations are affected, women two to three times more often than men. Onset may be at any age, most often between 25 and 50 yr.

Prominent immunologic abnormalities that may be important in pathogenesis include immune complexes found in joint fluid cells and in vasculitis. Plasma cells produce antibodies that contribute to these complexes. Lymphocytes that infiltrate the synovial tissue are primarily T helper cells, which can produce pro-inflammatory cytokines. Macrophages and their cytokines (e.g., tumor necrosis factor, granulocyte-macrophage colony-stimulating factor) are also abundant in diseased synovium. Increased adhesion molecules contribute to inflammatory cell emigration and retention in the synovial tissue. Increased macrophage-derived lining cells are prominent along with some lymphocytes and vascular changes in early disease.

In chronically affected joints, the normally delicate synovium develops many villous folds and thickens because of increased numbers and size of synovial lining cells and colonization by lymphocytes and plasma cells. The lining cells produce various materials, including collagenase and stromelysin, which can contribute to cartilage destruction; interleukin-1, which stimulates lymphocyte proliferation; and prostaglandins. The infiltrating cells, initially perivenular but later forming lymphoid follicles with germinal centers, synthesize interleukin-2, other cytokines, RF, and other immunoglobulins. Fibrin deposition, fibrosis, and necrosis also are present. Hyperplastic synovial tissue (pannus) may erode cartilage, subchondral bone, articular capsule, and ligaments. PMNs are not prominent in the synovium but often predominate in the synovial fluid.

Onset is usually insidious, with progressive joint involvement, but may be abrupt, with simultaneous inflammation in multiple joints. Tenderness in nearly all inflamed joints is the most sensitive physical finding. Synovial thickening, the most specific physical finding, eventually occurs in most involved joints. Symmetric involvement of small hand joints (especially proximal interphalangeal and metacarpophalangeal), foot joints (metatarsophalangeal), wrists, elbows, and ankles is typical, but initial manifestations may occur in any joint.

In some embodiments, the agent that promotes DSBR or that inhibits DNA-PKcs-directed apoptosis is co-administered with a therapy to treat the patient's condition. General classes of drugs commonly used in the non-antigen specific treatment of autoimmune disease include corticosteroids and disease modifying drugs. Corticosteroids have a short onset of action, but many disease modifying drugs take several weeks or months to demonstrate a clinical effect. These agents include methotrexate, leflunomide (ARAVA™), etanercept (ENBREL™), infliximab (REMICADE™), adalimumab (HUMIRA™), anakinra (KINERET™), rituximab (RITUXAN™), CTLA4-Ig (abatacept), antimalarials, gold salts, sulfasalazine, d-penicillamine, cyclosporin A, cyclophosphamide azathioprine; and the like.

Corticosteroids, e.g. prednisone, methylprednisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

Disease modifying anti-rheumatoid drugs, or DMARDs have been shown to alter the disease course and improve radiographic outcomes in RA. It will be understood by those of skill in the art that these drugs are also used in the treatment of other autoimmune diseases.

Methotrexate (MTX) is a frequent first-line agent because of its early onset of action (4-6 weeks), good efficacy, favorable toxicity profile, ease of administration, and low cost. MTX is the only conventional DMARD agent in which the majority of patients continue on therapy after 5 years. MTX is effective in reducing the signs and symptoms of RA, as well as slowing or halting radiographic damage. Although the immunosuppressive and cytotoxic effects of MTX are in part due to the inhibition of dihydrofolate reductase, the anti-inflammatory effects in rheumatoid arthritis appear to be related at least in part to interruption of adenosine and TNF pathways. The onset of action is 4 to 6 weeks, with 70% of patients having some response. A trial of 3 to 6 months is suggested.

Antimalarials such as hydroxychloroquine and chloroquine are rapidly absorbed, relatively safe, well-tolerated and often effective remittive agents for the treatment of rheumatoid arthritis, particularly mild to moderate disease. Hydroxychloroquine (Plaquenil, 200 mg tablets) is the drug of choice among antimalarials. The usual dose is 400 mg/day (6 mg/kg) but 600 mg/day is sometimes used. Normally it is prescribed as a single nighttime dose to avoid gastrointestinal symptoms. A period of 2 to 4 months is usual to take effect. A 6-month period without clinical effect should be considered a drug failure.

Sulfasalazine (SSZ) is another effective DMARD for the treatment of RA. Its mechanism of action in RA is unknown. Like the other DMARDs, it has been shown not only to reduce the signs and symptoms of RA but also to slow or halt radiographic progression. It can cause hypersensitivity reactions due to sulfa allergy, mild gastrointestinal, and occasionally, mild cytopenias. The usual dose is 2-3 grams per day in a twice daily dosing regimen. Blood monitoring is every 1-3 months depending on dose. Sulfasalazine is a good alternative to methotrexate for patients with liver disease.

The important 56-week Combination Therapy in Rheumatoid Arthritis (COBRA) trial demonstrated that step-down combination therapy with prednisolone, methotrexate, and sulfasalazine (SSZ) was superior to SSZ monotherapy for suppressing disease activity and progression of rheumatoid arthritis (RA). (COBRA: Arthritis Rheum. 2002 February; 46(2):347-56)

In a follow up study, the authors investigated whether the benefits of COBRA therapy were sustained over time, while the treating rheumatologists were not required to adhere to a pre-specified treatment protocol. Outcomes were analyzed on the basis of intent-to-treat, starting with data obtained at the last visit of the COBRA trial (56 weeks after baseline). After adjustment for differences in treatment and disease activity during follow-up, the differences between combination therapy-treated and control groups in regard to the rate of progression was statistically significant for each single year of follow up (4-5 years). The disability (based on the Health Assessment Questionnaire, HAQ) score did not change significantly over time. Independent baseline predictors of radiological progression over time (apart from treatment allocation) were rheumatoid factor positivity, radiographic scores (Sharp scores), and disease activity score (DAS28). The authors conclude that an initial 6-month cycle of intensive combination treatment that included high-dose corticosteroids resulted in sustained suppression of the rate of radiologic progression in patients with early RA, independent of subsequent antirheumatic therapy. The impressive results of this study suggest that aggressive combination therapy very early in the course of RA provides long-term benefit, even though the treatment course lasted only 6 months. However, the question of the role of newer biologicals such as TNF blockers and other targeted therapies in early RA (CTLA4Ig, IL-6R, etc) is not addressed by this trial. Additionally, acceptance of the complex COBRA medication is relatively low with both prescribing rheumatologists and RA patients in the Netherlands (Ann Rheum Dis. 2007 Mar. 28), underscoring the need for better biomarkers to predict response to individual drugs with greater potency but also the potential to cause serious side effects.

Also of concern is the potential for overtreatment of the subset of early arthritis patients who will experience a benign disease course. It is well established that a subset of early arthritis patients, including patients with early RA, will experience spontaneous natural remission in the absence of therapeutic intervention. Thus, biomarkers may be used to identify and differentiate such patients from patients who will develop full-blow and/or severe RA. Patients predicted to have benign and naturally remitting RA would likely be treated with NSAIDs and other "low-impact" therapies, while patients predicted to evolve to established RA would be treated more aggressively with DMARD therapy, and patients predicted to develop severe debilitating RA would be treated most aggressively with highly potent DMARD therapy.

Leflunomide (ARAVA™) was approved by the FDA and became available as a new DMARD agent for rheumatoid arthritis in October 1998. In clinical trials, its efficacy was similar to that of methotrexate and it represents a viable alternative to patients who have failed or are intolerant to methotrexate. Leflunomide has been demonstrated to slow radiographic progression and damage in RA. It can also be combined with methotrexate in patients with no preexisting liver disease, as long as the liver function tests are carefully monitored. The mechanism of action of leflunomide is not fully understood but may be related to its ability to inhibit tyrosine kinase activity and inhibit de novo pyrimidine biosynthesis through the inhibition of the enzyme dihydroorotate dehydrogenase. In vitro studies have demonstrated the inhibition of mitogen and IL-2 stimulated T cells. To achieve steady state, a loading dose of 100 mg daily for three days can be given followed by 20 mg daily. However, more recent recommendations are for a starting dose of 20 mg daily. The dose may be reduced to 10 mg daily if not tolerated or in patients having difficulty metabolizing or excreting the drug. Onset of action is in 4-8 weeks.

Tumor necrosis factor alpha (TNF-α, also referred to as TNF) is a pro-inflammatory cytokine produced by macrophages and lymphocytes. It is found in large quantities in the rheumatoid joint and is produced locally in the joint by synovial macrophages and lymphocytes infiltrating the joint synovium. Extensive clinical trial data have confirmed the efficacy of all three currently available TNF inhibitors in relieving the signs and symptoms of RA, and in slowing or halting radiographic damage. The strategies for inhibiting TNF that have been most extensively studied to date consist of monoclonal anti-TNF antibodies and soluble TNF receptors (sTNF-R). Both constructs will bind to circulating TNF-, thus limiting its ability to engage cell membrane-bound TNF receptors and activate inflammatory pathways. Soluble TNF-R, but not anti-TNF antibodies, also bind lymphotoxin.

One of the monoclonal anti-TNF antibodies is infliximab (REMICADE™), originally referred to as cA2. Infliximab is a chimeric human/mouse monoclonal anti-TNFα antibody composed of the constant regions of human (Hu) IgG1κ, coupled to the Fv region of a high-affinity neutralizing murine anti-huTNFα antibody. The antibody exhibits high affinity (Ka 1010/mol) for recombinant and natural huTNFα, and neutralizes TNF-mediated cytotoxicity and other functions in vitro. An alternate strategy has been to develop a fully human anti-TNF monoclonal antibody. One such antibody, known as D2E7, also known as adalumimab (HUMIRA™), was generated by phage display technology. A high affinity murine anti-TNF monoclonal antibody was used as a template for guided selection, which involves complete replacement of the murine heavy and light chains with human counterparts and subsequent optimization of the antigen-binding affinity. D2E7 (adalimumab, HUMIRA™) received FDA approval in December, 2002.

Alternatively, soluble TNF-R have been engineered as fusion proteins in which the extracellular ligand-binding portion of the huTNF-RI or huTNF-RII is coupled to a human immunoglobulin-like molecule. Although TNF-RI is thought to mediate most of the biological effects of TNF in vivo, engineered sTNF-RI and sTNF-RII constructs both appear to be effective in vivo inhibitors of TNF. Etanercept (sTNF-RII:Fc; ENBREL™) is the best studied of the sTNF-R and is approved for the treatment of rheumatoid arthritis in adults and in children. It is a dimeric construct in which two sTNF-RII (p75) are linked to the Fc portion of human IgG1. The dimeric receptor has a significantly higher affinity for TNFα than the monomeric receptor (50-1000-fold higher), and the linkage to the Fc structure significantly prolongs the half-life of the construct in vivo. Although it also has an unnatural linkage site, anti-etanercept antibodies have been infrequent. Another mechanism for prolonging the half-life of monomeric receptors is via conjugation with polyethylene glycol. One such construct, PEG-sTNF-RI (p55), has shown efficacy in several animal models of arthritis and is now in early clinical trials.

It is well established that only approximately ⅓ of patients exhibit a robust clinical response following initiation of any one of the 3 FDA-approved anti-TNF therapies (etanercept, adalimumab and remicade). As described below, clinical response is measured based on the American College of Rheumatology (ACR) response criteria (detailed below), and the ⅓ of patients that are experience robust clinical responses experience an ACR50 or greater response. A second ⅓ of patients experience a partial response to any one of the FDA approved agents, approximately an ACR20 response. The remaining ⅓ of RA patients exhibit no meaningful clinical response when initiated on an approved anti-TNF therapy. There is great clinical need for biomarkers to identify RA patients likely to respond vs. not respond to an anti-TNF agent given: (1) the potentially serious side effects of anti-TNF agents including (a) activation of tuberculosis, (b) increased rates of serious and life threatening infections, and (c) increased rates of demyelinating lesions; (2) the significant expense of anti-TNF therapies (approximately $15,000 USD per year of therapy), and (3) the availability of multiple other potential effective small molecule and biological agents (methotrexate, leuflonamide, anakinra, CTLAr-Ig).

As aforementioned, studies of early rheumatoid arthritis are critical to establish which drugs or combinations of drugs perform best to delay or prevent irreversible damage (see COBRA study above). An important ongoing study, The BeST study, focuses on different combinations of established DMARDs in conjunction with the TNF blocker infliximab (BeSt Study: Arthritis Rheum. 2005 November; 52(11):3381-90). This study aimed at comparing the efficiency of four treatment approaches to minimize disease progression in patients with early RA. Patients with active rheumatoid arthritis having symptoms of less than 2 years duration were randomized to one of four treatment arms: (1) Sequential monotherapy starting with methotrexate (MTX), then sulphasalazine (SSA), then leflunomide, then MTX with infliximab (IFX) (group 1, n=126); (2) Step-up combination therapy starting with MTX, then adding SSA, then hydroxychloroquine and then prednisone, then switching to MTX with IFX (group 2, n=121); (3) Initial combination therapy with MTX, SSA and a tapered high dose prednisone, then MTX with cyclosporin A and prednisone, then MTX with IFX (group 3, n=133); (3) Initial combination therapy with MTX and IFX, next leflunomide, then SSA, then MTX with cyclosporin A and prednisone (group 4, n=128). Better radiographic scores were observed in the more aggressive treatment arms (groups 3 and 4), supporting the call for early aggressive therapy. An important finding from the study is that similar clinical outcomes were achieved in all treatment groups when patients were followed by Disease Active Score (DAS) scoring and therapy was changed based on a protocol established before the trial had started. As underscored by previous clinical studies, rheumatologists need to quantify disease activity in response to therapy, regardless of which therapy is chosen. Biological markers to quantify such responses are highly sought after, to be used alone or in conjunction with established scoring systems. To monitor disease progression and response to therapy by means of biomarker signatures might be a critical addition to the clinical armamentarium of physicians for improved outcome measurement. The BeSt study is projected to last 5 years and will ultimately provide answers as to how early control of disease and choice of initial treatment might affect long-term outcome. Additional clinical trials in early RA with similar scope are underway or in the planning stages, involving a number of the novel biological DMARDs including MTX, anti-TNF agents, and CTLA4-Ig both as individual therapies as well as in combination (e.g. MTX; MTX+anti-TNF; anti-TNF; MTX+CTLA4-Ig; CTLA4-Ig). The performance of autoantibody and cytokine profiling studies as part of these early arthritis and early RAD MARD trials will further confirm and expand autoantibody and cytokine biomarker profiles for: (1) identifying patients that will benefit from DMARD therapy, and (2) guiding selection of the most appropriate and most effective DMARD for individual patients.

Soluble Interleukin-1 (IL-1) Receptor therapy. IL-1 is a cytokine that has immune and pro-inflammatory actions and has the ability to regulate its own expression by autoinduction. Evidence supports the fact that the level of disease activity in RA, and progression of joint destruction, correlate with plasma and synovial fluid levels of IL-1. IL-1ra is an endogenous receptor antagonist. Evidence supporting the anti-inflammatory role of IL-1ra in vivo is demonstrated by the observation that IL-1ra deficient mice spontaneously develop autoimmune diseases similar to rheumatoid arthritis and arthritis.

Anakinra (KINERET™) is a human recombinant IL-1 receptor antagonist (hu rIL-1ra) approved by the FDA for the treatment of RA. Anakinra can be used alone or in combination with DMARDs other than TNF blocking agents (Etanercept, Infliximab). Anakinra is a recombinant, nonglycosylated form of the human IL-1ra. It differs from the native nonglycosylated IL-1ra by the addition of an N-terminal methionine. Anakinra blocks the biologic activity of IL-1 by binding to IL-1R type I with the same affinity as IL-1. Usual time to effect is 2 to 4 weeks.

Cytotoxic T lymphocyte-associated antigen 4 (CTLA4) is an immunoregulatory protein expressed on the T cell surface after activation. It binds to CD80 or CD86, blocks their interaction with CD28, and thus acts as an off-switch for cell activation. CTLA4Ig is a genetically engineered fusion protein that consists of a human CTLA4 portion fused to a constant IgG1 region (also known as Abetacept, produced by Bristol-Myers Squib, New York City, N.Y., USA). This molecule binds to CD80 and CD86 and thereby inhibits T cell co-stimulation. Abetacept was approved by the US Food and Drug Administration for the treatment of RA. Like with anti-TNF agents only a minority of patients who had failed anti-TNF therapy exhibited significant clinical improvement in response to CTLA4-Ig therapy. These data suggest that subsets of RA patients with be responders and non-responders to therapy with CTLA4-Ig, and responsiveness will likely be determined by the underlying etiology of an individual patient's disease. Identification of autoantibody and cytokine biomarkers may identify molecular subtypes of RA that are responsive to agents such as CTLA4-Ig or anti-TNF.

Rituximab. The CD20 antigen is present on the cell surface of all pre-plasma cell stages of B cell differentiation. The mature plasma cell loses the CD20 antigen, and thus it serves as a relatively specific marker for B cells. Rituximab (Roche Pharmaceuticals, Basel, Switzerland; Genentech, South San Francisco, USA; IDEC Pharmaceuticals, San Diego, USA), a genetically engineered human-mouse chimeric monoclonal antibody against the CD20 antigen, binds to the CD20 antigen on the B cell surface and efficiently depletes B cells by antibody-dependent and complement-dependent cell lysis. As with anti-TNF agents and CTLA4-Ig only a minority of patient who failed anti-TNF therapy exhibited an ACR50 or greater response to rituximab therapy. Therapeutic monoclonal antibodies directed against other B cell surface antigens such as CD19, CD21 and CD22 are currently under development.

The most commonly used cytotoxic drugs for RA are azathioprine (IMURAN™), cyclophosphamide (CYTOXAN™) and cyclosporine A (SANDIMMUN™). Because the potential of high toxicity, these agents are utilized for life-threatening extra-articular manifestations of RA such as systemic vasculitis or severe articular disease refractory to other therapy. It is recommended that these agents be used under the direction of a rheumatologist. Azathioprine is a purine analog. Cyclophosphamide is an alkylating agent. Cyclosporine is an immunosuppressive agent approved for use in preventing renal and liver allograft rejection. Cyclosporine inhibits T cell function by inhibiting transcription of interleukin-2. Main toxicity's include infection and renal insufficiency.

Interleukin-6 is a glycoprotein composed of 184 amino acids. Numerous cells can produce this inducible cytokine, including macrophages, B cells, T cells, fibroblasts, endothelial cells, mesangial cells, and many types of tumor cells. The effects of IL-6 are pleiotropic, occurring at both a systemic and a local tissue level, and involving a wide variety of cells. Of particular relevance to RA are the effects on the differentiation of B and T lymphocytes, as well as the differentiation of macrophages, megakaryocytes, and osteoclasts. Interleukin-6 is elevated in the serum and synovial fluid in RA patients. The excessive production of IL-6 is postulated to play a role in the pathogenesis of several inflammatory diseases such as RA, Crohn's disease, and juvenile idiopathic arthritis. In RA, IL-6 participates in immune cell activation and autoantibody production, osteoclastogenesis, and bone loss, and the often debilitating systemic and constitutional symptoms associated with the acute-phase response. MRA (Chugai Pharmaceutical Co. Ltd., Tokyo, Japan) is a humanized anti-IL-6 receptor antibody (Tocilizumab) that inhibits the binding of IL-6 to its receptor IL-6R and prevents IL-6 signal transduction.

Trials targeting other cytokines, including IL-12, IL-15, IL-18, and p19 subunit of IL-23 (Eli Lilly) are in early clinical development. AMG 714 (GENMAB™, Copenhagen, Denmark) is a human monoclonal antibody that binds to IL-15 and inhibits its signaling. Patients receiving AMG 714 had clinically meaningful improvement compared with placebo, demonstrating that IL-15 is a target in the treatment of RA. In preclinical studies, an anti-IL-17 antibody significantly reduced the severity of collagen-induced arthritis. BlyS, or BAFF, is a member of the tumor necrosis factor family of cytokines, and its receptors, BCMA, BAFFR, and TACI, are largely restricted to B cells (a small amount of TACI has been found on activated T cells). LymphoStat-B is a fully human IgG1λ monoclonal antibody that neutralizes human BlyS. The administration of LymphoStat-B to cynomolgus monkeys selectively reduces B cells in blood and tissue with no overt toxicity. Natalizumab (TYSABRI™, Biogen) is a monoclonal antibody specific for alpha-4-integrin and blocks the homing of white blood cells into tissues. Natalizumab was recently FDA approved for MS.
Screening Methods.

The methods described above provide a useful system for screening candidate agents for activity in improving immune system function in an individual with a condition in which lymphocytes have elevated amounts of DNA double strand breaks (DSB) relative to a normal control, e.g. Rheumatoid Arthritis, following a bone marrow transplant, or in people aged about 50 or more. To that end, it has been shown that elevated numbers of double strand breaks sensitizes naïve lymphocytes to DNA-PKcs-directed apoptosis. Accordingly, screening for candidate agents that prevent apoptosis in cells with elevated amounts of DSBs should identify agents that will be useful in protecting those cells from apoptosis, which, in turn, will improve immune system function in patients with conditions characterized by an immune system comprising lymphocytes having elevated amounts of DNA double strand breaks (DSB) relative to a normal control.

In screening assays for biologically active agents, cells having double strand breaks, usually cultures of cells having elevated levels of double strand breaks, are contacted with a candidate agent of interest and the effect of the candidate agent is assessed by monitoring one or more output parameters. These output parameters may be reflective of an apoptotic state, such as the amount of phosphorylation of JNK family members, the amount of DNA fragmentation, the amount of cell blebbing, the amount of phosphatidylserine on the cell surface as visualized by Annexin V staining, and the like by methods described above. Alternatively or additionally, the output parameters may be reflective of the viability of the culture, e.g. the number of cells in the culture, the rate of proliferation of the culture. Alternatively or additionally, the output parameters may be reflective of the function of the cells in the culture, e.g. the cytokines and chemokines produced by the cells, the rate of chemotaxis of the cells, the cytotoxic activity of the cells, etc.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Cells useful for screening include any cell that has elevated numbers of double strand breaks relative to a normal control. For example, the cell may be a fibroblast that has been treated by methods known in the art to promote double strand breaks, e.g. irradiation with ionizing radiation, or treatment with $H_2O_2$ as described above. As another example, the cell may be acutely cultured from an individual that has a condition in which lymphocytes have elevated amounts of DNA double strand breaks (DSB) relative to a normal control, e.g. Rheumatoid Arthritis or a bone marrow transplant.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype. In some embodiments, the cells are also contacted with an agent that suppresses DSBR, further sensitizing the cells to the apoptotic effects of the elevated numbers of DSBs.

Various methods can be utilized for quantifying the selected parameters. For example, western blots or protein arrays may be employed to measure phosphorylation of the JNK family members. Terminal deoxynucleotidyl transferase dUTP nick end labeling (TUNEL) may be employed to measure DNA fragmentation. Flow cytometry may be employed to detect Annexin V binding to phosphatidylserine on the cell surface. BrdU labeling may be employed to detect proliferation rates. Western blots may be employed to assay cytokines and chemokines secreted into the medium. Migration assays, e.g. in Boyden chambers, may be employed to assay chemotaxis capacity. Antibody-dependent cell-mediated cytotoxicity (ADCC) assays may be employed to assay cytotoxicity of cells. Such methods would be well known to one of ordinary skill in the art.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

In rheumatoid arthritis (RA), the process of T-cell aging is accelerated (Goronzy J J and Weyand C M (2005) Immunol Rev 204: 55-73; Weyand C M, et al. (2009) Nature Review Rheumatology 5(10): 583-588). Telomeres of CD4 T cells are age-inappropriately shortened and clonal populations of CD28-deficient T cells accumulate (Koetz K, et al. (2000) Proc Natl Acad Sci USA 97(16): 9203-9208; Schonland S O, et al. (2003) Proc Natl Acad Sci USA 100(23): 13471-13476). Premature senescence not only involves memory T cells engaged in chronic inflammatory lesions, but is most pronounced among naïve T cells unprimed by antigen. Two recent studies have identified novel mechanisms causing premature immunosenescence in RA (Fujii H, et al. (2009) Proc Natl Acad Sci USA 106(11): 4360-4365; Shao L, et al. (2009) J Exp Med 206(6): 1435-1449). Naïve RA T cells were found to be apoptosis susceptible, a defect mechanistically linked to insufficiency of the enzyme telomerase (Fujii H, et al. (2009) Proc Natl Acad Sci USA 106(11): 4360-4365). When undergoing priming, survival rates of RA T-cells reached only half of those in control T-cells and overexpression of hTERT, the protein component of telomerase, rescued RA T cells from death. Also, naïve RA T cells were characterized by the accumulation of DNA double strand breaks, a defect caused by the inadequate production of the ataxia telangiectasia mutated gene product (ATM), an enzyme critically involved in recognizing DNA double strand breaks (Shao L, et al. (2009) J Exp Med 206(6): 1435-1449). Forced overexpression of ATM in RA T cells restored DNA repair and T cell survival.

Apoptotic susceptibility of naïve T cells determines the generation of sufficient antigen-specific clones as well as the cellular yield of homeostatic proliferation, a process that generates new T cells. Homeostatic T-cell proliferation is particularly relevant in individuals over the age of 50 years, when thymic T-cell production has ceased. RA incidence rates are highest during the 7th and 8th decades of life when homeostatic proliferation is most needed for T-cell regeneration and maintenance (Doran M F, et al. (2002) Arthritis Rheum 46(3): 625-631; Goronzy J J, et al. (2005) Ann N Y Acad Sci 1062: 182-194).

How insufficiency for telomerase and ATM mediates the apoptotic sensitivity of T cells is not understood. Proliferating naïve T cells are resistant to death ligand-death receptor-mediated apoptosis, but forced overexpression of Bcl-2 protects T cells from dying, pointing towards cell-internal signals as apoptosis initiators (Fujii H, et al. (2009) Proc Natl Acad Sci USA 106(11): 4360-4365). One of the most effective stress signals linked to apoptosis is damaged DNA, considered particularly important in senescent cells that have been chronically exposed to stressors, e.g. endogenously generated reactive oxygen species. Depending on the type of DNA damage cells have several options to detect and repair broken DNA and similar pathways may be involved in surveillance of telomeric structures (Denchi E L, et al. (2007) Nature 448(7157): 1068-1071; Riha K, et al. (2006) Annu Rev Genet. 40: 237-277; Verdun R E, et al. (2006) Cell 127(4): 709-720). In mammalian cells, two major pathways repair DNA double strand breaks (DSB): nonhomologous end-joining (NHEJ) and homology-directed repair (HDR). Three of the DNA damage sensors involved in these pathways are PI3K-related kinases: ATM, the ataxia telangiectasia-related (ATR), and the catalytic subunit of DNA-dependent protein kinase (DNA-PKcs) (Falck J, et al. (2005) Nature 434(7033): 605-611). ATM orchestrates HDR by interacting with the DNA-damage sensing MRE11-Rad50-NBS1 (MRN) complex, phosphorylates multiple target molecules, and activates cell cycle checkpoints to arrest the cell cycle and allow for fixing of the DNA (Lavin M F (2007) Oncogene 26(56): 7749-7758). One of the ATM targets is p53, which facilitates cell death if DNA repair fails (Lavin M F, et al. (2007) Cell Cycle 6(8): 931-942). The first step in NHEJ is the detection of fragmented DNA by Ku70/Ku80, which translocates inward from the DNA end to make the DNA termini accessible to DNA-PKcs (Lees-Miller S P, et al. (2003) Biochimie 85(11): 1161-1173). Cells deficient in DNA-PKcs are highly sensitive to radiation-induced cell death (Meek K, et al. (2008) Adv Immunol 99: 33-58) and animals with DNA-PKcs deficiency typically have severe combined immunodeficiency (Meek K, et al. (2004) Immunol Rev 200: 132-141). DNA-PKcs is not only involved in sensing/repairing DSB, but may be equally important as a repair protein in telomeric end-capping (Bailey S M, et al. (1999) Proc Natl Acad Sci USA 96(26): 14899-14904; Williams E S, et al. (2009) Cancer Res 69(5): 2100-2107). Proteins participating in the recognition and handling of double-stranded DNA ends, either at the telomeric end or in DSB, may be largely overlapping. RA T cells, impaired in inducing sufficient telomerase and deficient in utilizing the ATM-MRE11-p53 pathway, should be a valuable model system to investigate the role of dysfunctional telomeres and unrepaired DNA in inducing DNA repair activity.

The study described below was designed to identify cell-internal signals that render RA T cells apoptosis susceptible, with particular emphasis on the involvement of DNA repair mechanisms in making T-cell fate decisions. To exclude interfering mechanisms of T-cell death by external death signals, these studies were focused on naïve CD4 T cells, which are typically resistant to Fas-FasL-mediated apoptosis (Fujii H, et al. (2009) Proc Natl Acad Sci USA 106(11): 4360-4365; Krammer P H, et al. (2007) Nat Rev Immunol 7(7): 532-542). Naïve CD4 T cells from RA patients have a spontaneous apoptosis rate twice as high as in age-matched control individuals. Resting naïve T cells progressively accumulate oxidative DNA damage and undergo apoptosis, a process accelerated in RA T cells. Apoptotic loss of resting T cells is independent from activation of the ATM-p53 pathway. Instead, RA T cells upregulate DNA-PKcs. Inhibition of DNA-PKcs activity or knockdown of the DNA-PKcs gene rescues RA T cells from death. Protection from excessive apoptosis is also achieved by inhibiting the JNK signaling pathway. Among the BH3-only proapoptotic Bcl-2 family members, Bmf and Bim transcripts and protein are selectively upregulated in RA T cells, suggesting that Bmf and Bim may be crucial in sensing and relaying stress signals. Targeting the DNA-PKcs-JNK-Bim axis may provide a novel therapeutic intervention to restore T-cell homeostasis in RA.

Materials and Methods

Patients.

The study group included 86 RA patients and 76 control subjects. RA patients fulfilled the ACR criteria, and all were positive for rheumatoid factor. Control subjects were matched for age and ethnicity; had no personal or family history of autoimmune disease. A history of cancer or chronic viral infection was considered an exclusion criterion. Demographic characteristics of RA patients and controls are summarized in Tables I and II. Patients with systemic lupus erythematosus (SLE) were selected for having active disease. Their demographic characteristics are given in Table III. The study was approved by the Institutional Review Board, and all subjects gave appropriate informed consent.

TABLE I

Demographic characteristics of study populations.

| Characteristics | Controls | RA | P Value |
|---|---|---|---|
| Number of subjects | 76 | 86 | |
| Female/Male[a] | 62/14 | 68/18 | 0.61 |
| Age (mean ± SD years)[a] | 46.8 ± 10.4 | 49.5 ± 13.6 | 0.17 |
| Ethnicity[a] | | | |
| African American | 46 | 53 | |
| White | 23 | 18 | |
| Hispanic | 7 | 15 | |

[a]No significant difference

TABLE II

Clinical characteristics of RA patients

| Characteristics | Values |
|---|---|
| Disease duration (mean ± SD years) | 7.4 ± 7.5 |
| Active disease[a] | 66.2% |
| Tobacco use | 18.6% |
| Extraarticular manifestations | 36.1% |
| ESR, mm/hour | 37.6 |
| DMARD naïve | 8.2% |
| Medications | |
| Corticosteroids | 67.5% |
| Methotrexate | 67.9% |
| Hydroxychloroquine | 46.5% |
| Leflunomide | 8.2% |
| TNF inhibitors | 16.3% |

ESR, erythrocyte sedimentation rate; DMARD, disease-modifying antirheumatic drugs; DD, disease duration
[a]Active disease defined by FDA criteria [presence of three or more of the following: morning stiffness (>45 min), swollen joints (>3 min), tender joints (>6 min), and sedimentation rate (>20 mm)]

TABLE III

Demographic characteristics of SLE population.

| Characteristics | Controls | SLE |
|---|---|---|
| Number of subjects | 11 | 13 |
| Female/Male | 9/2 | 11/2 |
| Age (mean SD years) | 42.9 ± 15.1 | 40.1 ± 9.9 |
| Ethnicity | | |
| African American | 81.8% | 84.6% |
| White | 18.2% | 15.4% |

Cell Purification and Cell Culture.

Peripheral blood mononuclear cells (PBMC) were separated from whole blood with Lymphocyte Separation Medium (Mediatech Inc., Herndon, Va.). CD45RO⁻ cells were negatively selected with microbeads (Miltenyi Biotec Inc., Auburn, Calif.), and the naïve CD4⁺CD45RO⁻ population was subsequently selected with CD4 microbeads (autoMACS, Miltenyi Biotec Inc.).

CD4⁺CD45RO⁻ T cells were maintained in a resting state in DMEM without mitogenic stimulation for three days. In selected experiments, T-cell homeostatic cytokines were supplemented. To test for the role of signaling networks in mediating apoptosis, the following inhibitors were added to the cultures at day 0: DNA-PKcs inhibitor IC86621 (Sigma-Aldrich, St. Louis, Mo.), JNK inhibitor II (Calbiochem, La Jolla, Calif.), p38 inhibitor (Alexis Biochemicals, Plymouth Meeting, Pa., SB203580), CaM inhibitor (Calbiochem), NF-KB inhibitor (Calbiochem), and AKT inhibitor (Calbiochem).

To induce DNA damage, naïve CD4 T cells were incubated in DMEM containing 0, 56, 112, or 224 μM $H_2O_2$ for 1 h. After a brief rinse in medium, cells were collected for DNA damage analysis or kept for an additional 3 h before DNA-PKcs transcripts were quantified.

Comet Assay.

DNA damage was quantified with CometAssay™ kits (R&D Systems, Minneapolis, Minn.), modified as previously described (Shao L, et al. (2009) J Exp Med 206(6): 1435-1449). Cells (1×10⁵/ml) mixed with molten LMAgarose (1:10 at 37° C.) were immediately transferred onto a CometSlide, kept in the dark for 10 min in a flat position, immersed in cold lysis solution (2.5 M NaCl, 100 mM EDTA, 10 mM Tris base, 1% sodium lauryl sarcosinate, 1% Triton-100, 10% DMSO) for 60 min, and treated with freshly prepared alkaline solution (300 mM NaOH, 1 mM EDTA, pH>13) for 20 min at room temperature. After washing twice in 1×TBE buffer for 5 min, slides were transferred to a horizontal electrophoresis chamber and aligned at equidistance from the electrodes. One volt/cm was applied for 10 min. Stained slides (20 µg/ml ethidium bromide) were analyzed by fluorescence microscopy. A minimum of 50 cells were evaluated in each sample using the CometScore™ software (TriTek Corp., Morrisville, Va.).

DNA damage was quantified by the tail moment (TM) calculated as percentage of DNA in the tail×tail length) (Hellman B, et al. (1995) Mutat Res 336(2): 123-131).

Flow Cytometry.

To quantify T-cell apoptosis, CD4$^+$CD45RO$^-$ cells were washed and suspended in 500 µl FACS buffer supplemented with EasyComp Blank Particles (Spherotech, Lake Forest, Ill.). Uptake of PI (Sigma-Aldrich) was determined by flow cytometry. Apoptotic cells were detected with PE-Annexin V (BD Biosciences, San Jose, Calif.) and 7-AAD (BD Biosciences).

For intracellular staining, cells were fixed directly with 1.5% formaldehyde for 10 min at room temperature and resuspended in 90% methanol. After overnight incubation, $10^7$ cells/ml were stained with FITC-pATM (Rockland Immunochemicals, Gilbertsville, Pa.), Alexa Fluor 488-pp53, FITC-Bcl-2, FITC-pJNK, Alexa Fluor 488-labeled anti-Bim, PE-labeled anti-Bmf, (all Cell Signaling), Alexa Fluoro 488-Ku70 (Santa Cruz Biotechnology, Santa Cruz, Calif.) antibodies, or FITC-conjugated 8-oxoguanine probe (OxyDNA Assay Kit; Calbiochem). Proteins or 8-oxoguanine expression were detected by an LSRII flow cytometer (BD Biosciences). Data were analyzed by FlowJo software (Tree Star Inc., Ashland, Oreg.).

DNA Isolation and Quantitative PCR.

Total RNA was extracted from $1.0 \times 10^5$ cells, and cDNA was synthesized with AMV-reverse transcriptase and random hexamer primers. PCR was conducted as previously described. Primer sequences are shown in Table IV.

Quantitative reverse transcription PCRs were completed in triplicate following previously described protocols (Niessner A, et al. (2006) Circulation 114(23): 2482-2489). Expression levels were determined by interpolation with a standard curve. cDNA copies were adjusted for $1 \times 10^8$ ribosomal RNA copies.

TABLE IV

Primer sequences.

| Gene | Primer sequence | SEQ ID NO |
|---|---|---|
| 18S ribosomal RNA | 5'-AGGAATTCCCAGTAAGTGCG-3' | 1 |
| | 5'-GCCTCACTAAACCATCCAA-3' | 2 |
| DNA-PKcs | 5'-CTTTGTCGTGTGGAGGGAA-3' | 3 |
| | 5'-CACAACGGGGTTCAGAAGTT-3' | 4 |
| Puma | 5'-GGACGACCTCAACGCACAGTA-3' | 5 |
| | 5'-GGCAGGAGTCCCATGATGAGA-3' | 6 |
| Noxa | 5'-CCTGGGAAGAAGGCGCG-3' | 7 |
| | 5'-TCAGGTTCCTGTGCAGAA G-3 | 8 |
| Bim | 5'-ACGCTTACTATGCAAGGAGGG-3' | 9 |
| | 5'-GGTCTTCGGCTGCTTGGTAAT-3' | 10 |

TABLE IV -continued

Primer sequences.

| Gene | Primer sequence | SEQ ID NO |
|---|---|---|
| Bmf | 5'-CTGCACAACCTTGCTTTGAA-3' | 11 |
| | 5'-CAAGGGCCTGACAGAGAAAG-3' | 12 |

Western Blot.

Whole cell lysates were prepared in RIPA buffer (Cell Signaling Technology, Danvers, Mass.) plus PMSF and a protease inhibitor cocktail (Sigma). For each sample, equal amounts of total protein were electrophoresed, transferred to a nitrocellulose membrane (Amersham, Piscataway, N.J.), and blocked with 5% nonfat milk. Antibodies specific for DNA-PKcs, pDNA-PKcs, JNK (1:1000, Santa Cruz), and pJNK (Cell Signaling) were added overnight at 4° C., followed by washing with washing buffer. Membranes were subsequently incubated with secondary antibodies (1:6000; Santa Cruz) for 1 h at room temperature and developed with a chemiluminescent detection system (GE Healthcare, Buckinghamshire, UK). To ensure equal loading, membranes were stripped and reprobed for β-actin using goat anti-human actin antibodies (1:4000; Santa Cruz).

siRNA Transfection.

DNA-PKcs siRNA (sc-35200) was purchased from Santa Cruz, Calif. Six micrograms of siRNA oligonucleotides were transfected into resting CD4 T cells using the Amaxa Nucleofector® system and Human T-cell Nucleofector® kits (Amaxa, Fremont, Calif.) as previously described (Shao L, et al. (2009) J Exp Med 206(6): 1435-1449). AllStars Negative Control siRNA (Qiagen) served as a control. Twenty-four hours after transfection, knockdown efficiencies were monitored by qPCR and Western blotting.

Detection of 53BP1 Foci.

CD4$^+$CD45RO$^-$ T cells were maintained in DMEM without mitogenic stimulation for 72 h. Immunofluorescence staining was performed as previously published (Song H, et al. (2007) Nat Cell Biol 9(5): 573-580). T cells were incubated in cytoskeleton buffer (10 mM PIPES at pH 6.8, 100 mM NaCl, 300 mM sucrose, 3 mM MgCl$_2$, 1 mM EGTA, 0.5% Triton X-100) for 5 min on ice, followed by incubation in cytoskeleton stripping buffer (10 mM Tris-HCl at pH 7.4, 10 mM NaCl, 3 mM MgCl$_2$, 1% Tween 40, 0.5% sodium deoxycholate) for 5 min on ice and then cells were fixed with fixation buffer (3.7% formaldehyde in 1×PBS). The fixed cells were blocked with 1% BSA in PBS for 30 min at 37° C. and incubated with a rabbit polyclonal antibody against 53BP1 for 1 h at room temperature. The cells were washed three times in PBS, incubated with secondary antibodies for 1 h at room temperature, washed and stained with DAPI. Images were acquired with a confocal laser-scanning inverted microscope (LSM 510 META Axiovert 200; Carl Zeiss, Inc.).

Statistical Analysis.

Groups were compared using parametric tests for independent or paired samples as appropriate. Results are expressed as the mean±SEM. P values of less than 0.05 were considered significant.

Results

In Rheumatoid Arthritis, Resting CD4 T Cells are Prone to Apoptosis.

Figure 1:
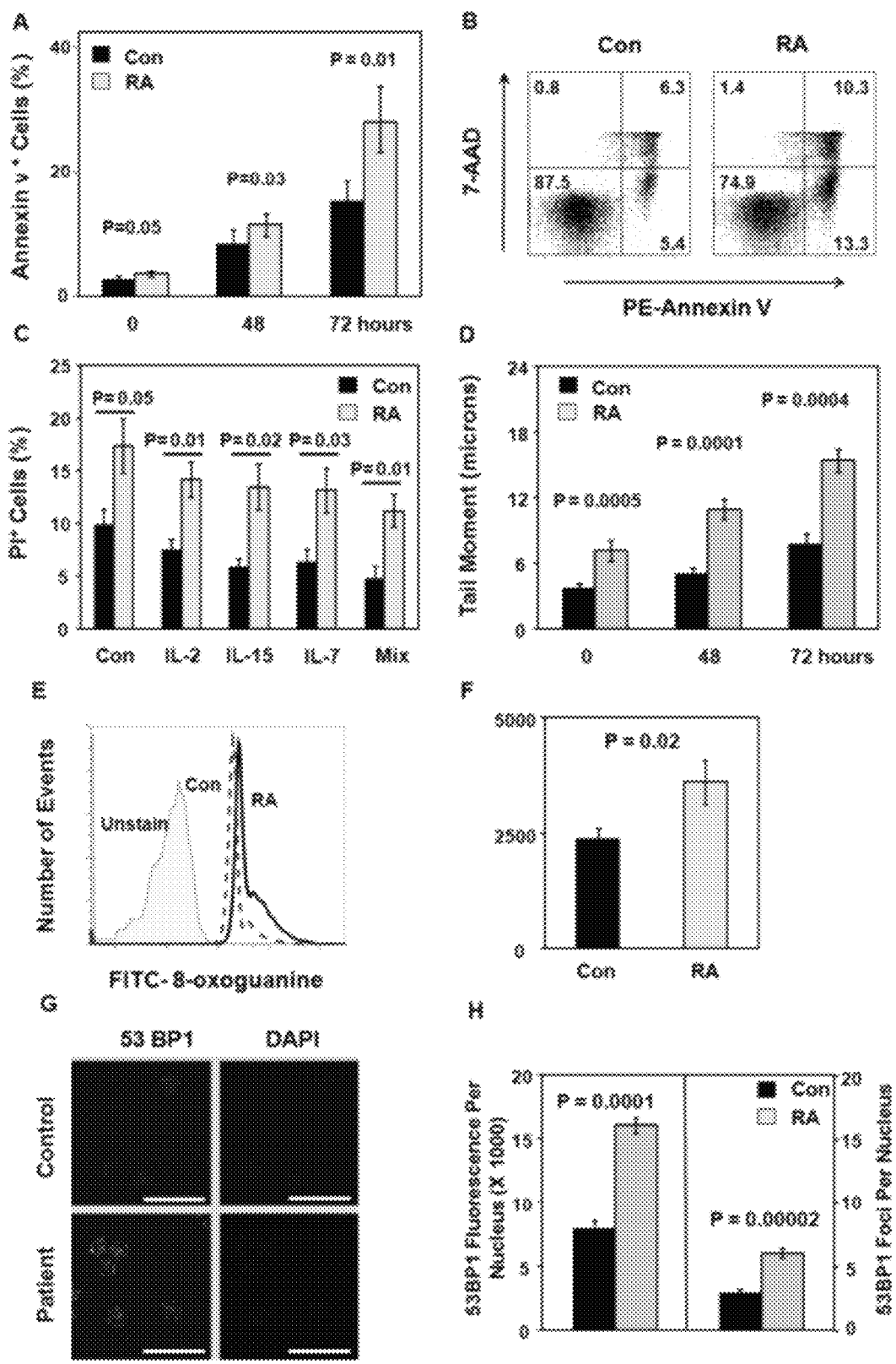
FIG. 1. Apoptotic susceptibility and DNA damage in naïve CD4 T cells from RA patients. CD4+CD45RO− T cells were isolated from the peripheral blood of RA patients and controls. Cells were maintained in culture without mitogenic stimulation for 72 h. (A) T cells undergoing apoptosis were identified by Annexin V and 7-AAD staining in patient-derived and control samples. Data are given as mean±SEM from 6 patients and 6 controls. (B) Representative data from one patient and one control collected after 72 h are shown. (C) Cells were maintained in culture with IL-2 (20 U/ml), IL-7 (20 ng/ml), IL-15 (10 ng/ml), or a mixture of the three (Mix) for 72 h. T cells undergoing apoptosis were identified by PI staining. Data are given as mean±SEM from 7 patients and 5 controls. (D) DNA breaks were quantified by comet assay after 72 h. Data are given as mean±SEM of 7 patients and 6 controls with a minimum of 90 individual cells analyzed in each sample. (E) Flow cytometry analysis of 8-oxoguanine levels in control (dashed line) and RA T cells (solid line). Unstained control is shown as light grey. (F) The level of 8-oxoguanine in 5 RA and 5 control samples is given as mean fluorescence intensity (MFI) of FITC-8-oxoguanine±SEM. (G) 53BP1 foci were determined by immunofluorescence staining and confocal laser microscopy after 72 h. Bar, 20 μM (H) The levels of 53BP1 foci in 3 RA and 3 control samples is given as total 53BP1 intensity per nucleus±SEM and 53BP1 foci per nucleus±SEM.

In vivo the vast majority of CD4 T cells is in a resting state and, accordingly, is not undergoing apoptosis. In normal healthy donors, only 2.6% of freshly isolated naïve CD4 T cells express Annexin V. In RA patients, the rate of spontaneous apoptosis is significantly higher (3.53% Annexin V+ cells, p=0.05) (FIG. 1A, B). When removed from their natural resources and kept ex vivo, human T cells progressively die. By 72 h, 15% of T cells from control donors display apoptotic features (FIG. 1A, B). The susceptibility to undergo apoptosis is significantly higher in RA T cells with death rates of 25-30% (p=0.01).

T-cell survival may depend on the availability of growth-promoting cytokines (IL-2, IL-7, IL-15) (Ma A, et al. (2006) Annu Rev Immunol 24: 657-679; Surh C D, et al. (2008) Immunity 29(6): 848-862). Therefore, T cells were supplemented with IL-2, IL-7, IL-15, or a mixture of all three cytokines. Optimal doses were determined in pilot experiments. IL-2, IL-7, and IL-15 reduced apoptosis rates with about equal potency, but prevented only one-third of the T-cell attrition (FIG. 1C). Anti-apoptotic effects of the cytokines were similar in control and RA T cells and could not abolish the difference in apoptosis between patients and controls.

To identify death-inducing signals, different from cytokine withdrawal, the load of damaged DNA was determined. In the absence of mitogenic or antigenic stimulation, levels of oxidatively damaged DNA detected as 8-oxoguanine bases by flow cytometry were low in almost all control T cells (FIG. 1D). RA T cells contained significantly higher levels of 8-oxoguanine DNA lesions, often displaying a biphasic flow cytometry pattern indicative of a cell subpopulation with markedly elevated signals for 8-oxoguanine sites. In naïve CD4 T cells from RA patients, fluorescence intensities marking oxidized DNA were 1.5-fold higher than in controls (FIG. 1E, p=0.02).

To search for DNA DSB, comet assays were employed to examine purified CD4CD45RO− T-cell populations immediately after isolation and 48 and 72 h later (FIG. 1F). Tail moments were low in fresh T cells, but continuously increased over the 72 h observation period. The load of DNA breaks was almost twice as high in RA T cells (p<0.001, p=0.0001, p<0.001), with a steeper slope of accumulation over the 3-day culture.

Accumulation of DNA DSB was confirmed by immunostaining for 53BP1 foci in the nuclei of RA and control T cells. Quantification of immunofluorescence staining showed significant higher anti-53BP1 binding in the nucleus of RA T cells (FIG. 1G) and a higher number of 53BP1 foci per nucleus. In essence, spontaneous apoptosis in naïve CD4 T cells was closely correlated with the accrual of damaged DNA.

RA T Cells Die Independently of the ATM-p53 Pathway.

Figure 2:
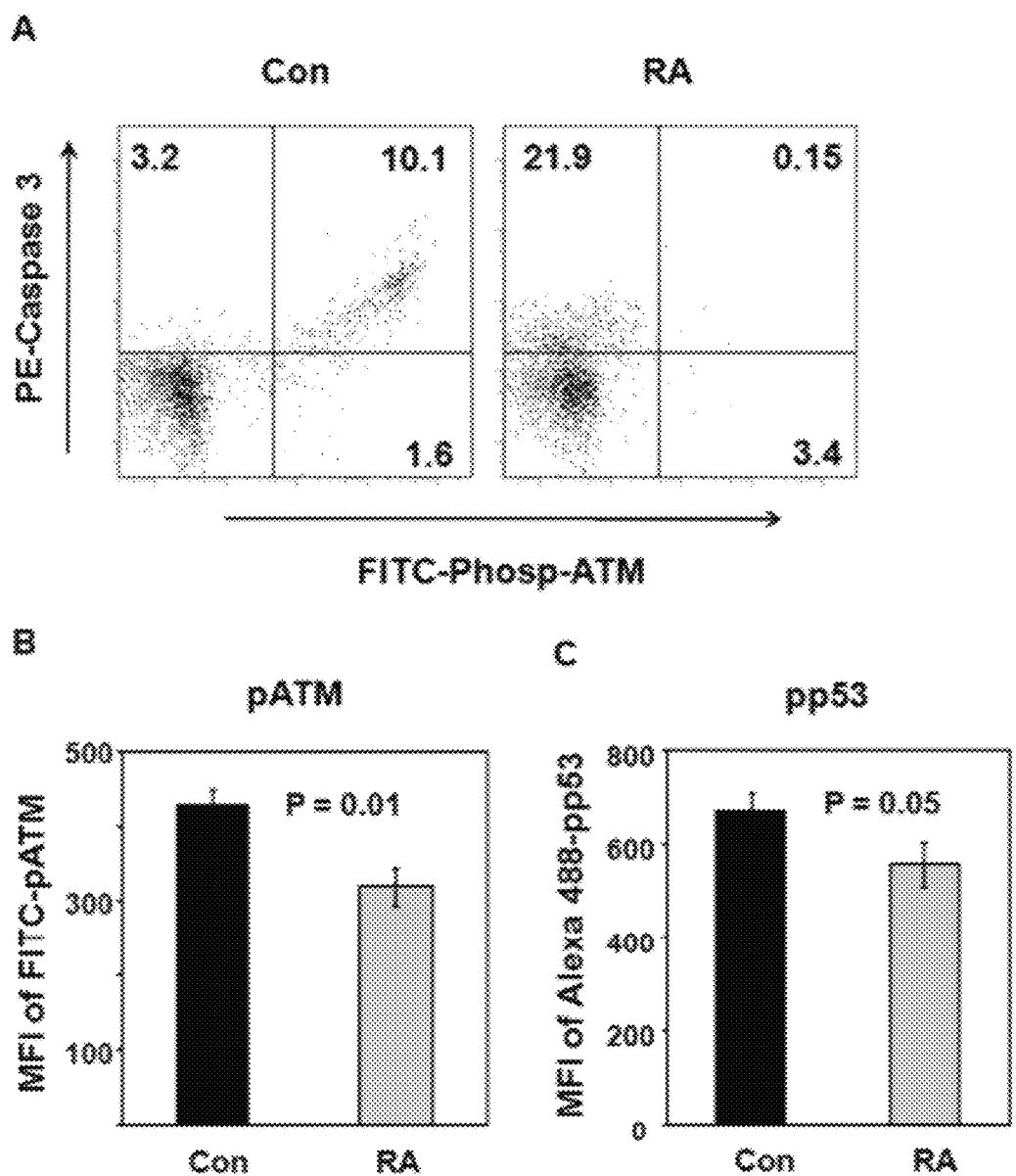
FIG. 2. Apoptosis in RA CD4 T cells is ATM and p53 independent. CD4+CD45RO− T cells were isolated from 6 controls and 6 RA patients. Cells were maintained in culture without stimulation and collected after 72 h. (A) T cells undergoing apoptosis were stained with PE-caspase-3 and phosphorylated ATM was detected by FITC-Phosp-ATM. Representative cytometric data from one patient and one control are shown. (B) Expression levels of pATM were quantified by flow cytometry in 5 RA and 5 control samples and are given as mean MFI of FITC-pATM±SEM. (C) Expression levels of pp53 were quantified by flow cytometry in 6 RA and 6 control samples and are given as mean MFI of Alexa Fluor 488-pp53±SEM.

T cells with fragmented DNA are culled from the pool of DNA damage sensing and repair mechanisms fail to restore genomic intactness. The most lethal DNA lesions are DSB which upon recognition by the DNA repair machinery elicit cell cycle arrest to allow for repair. One of the major downstream targets of ATM is p53, which facilitates cell death in case repair is insufficient. Given the increased prevalence of DSB and oxidized DNA lesions in RA T cells, we analyzed the expression of pATM and pp53 in paired samples of control and RA naïve CD4 T cells (FIG. 2). Among control T cells, essentially all cells with activated caspase-3 expressed pATM, suggesting that the ATM-p53 pathway controls apoptosis of most healthy CD4 T cells. In contrast, patient-derived CD4 T cells undergoing apoptosis and expressing activated caspase-3 lacked pATM expression. Decreased expression of pATM and pp53 was confirmed in a comparative analysis of control and patient-derived samples demonstrating decreased expression of both pATM and p53 in the RA T cells (FIG. 2B, p=0.01 and FIG. 2C, p=0.05). These data indicate an ATM-p53-independent pathway mediates T-cell apoptosis in RA.

Spontaneous Upregulation of the DNA Damage Sensing Enzyme DNA-PKcs.

Figure 3:
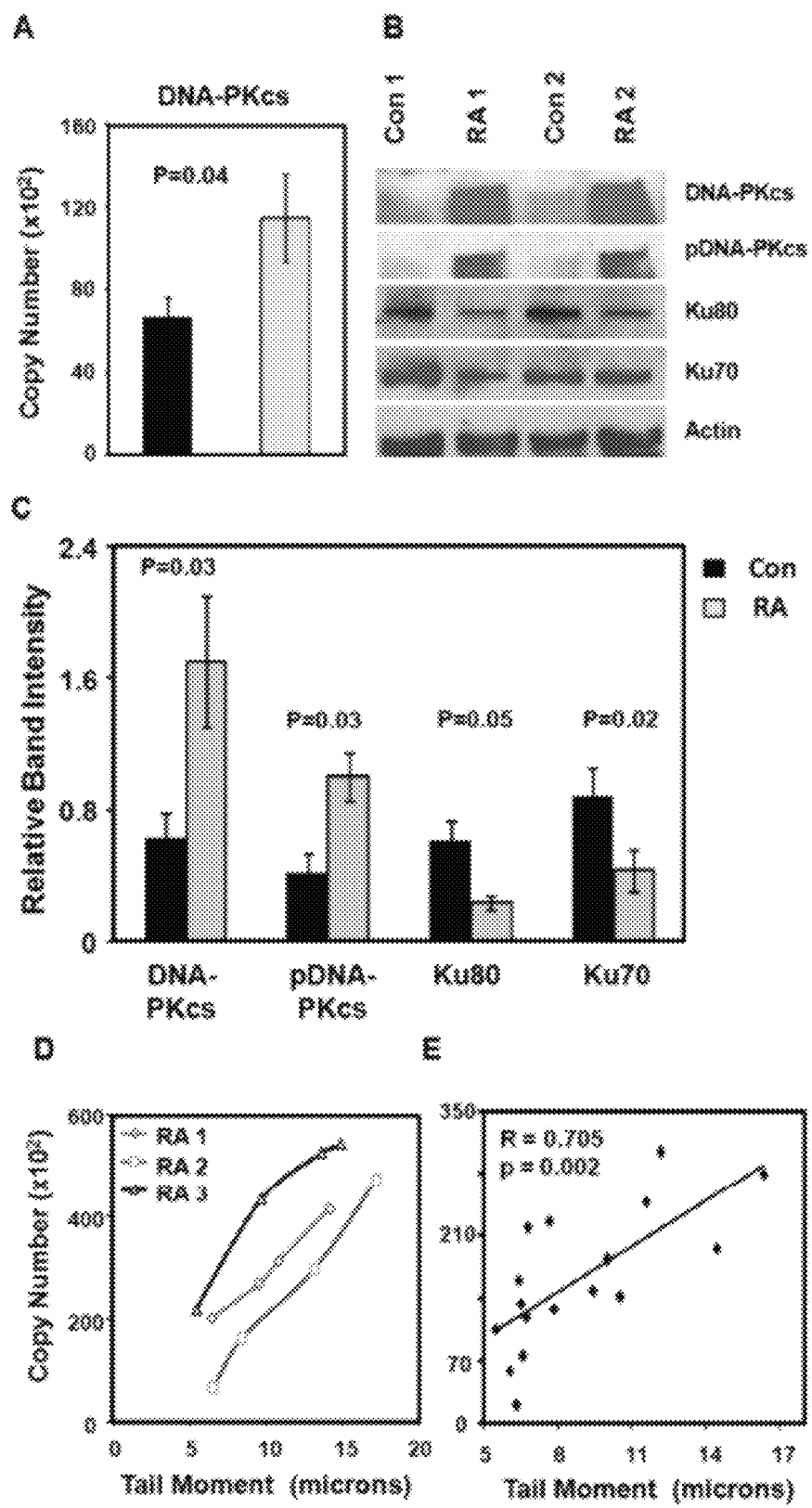
FIG. 3. RA CD4 T cells express increased levels of DNA-PKcs but decreased levels of Ku70 and Ku80. CD4+ CD45RO− T cells were purified from RA patients and age-matched controls. Cells were analyzed immediately after isolation and after 72 h of culture without stimulation. (A) DNA-PKcs transcript levels were measured by RT-PCR in control (black bar) and RA T cells (light grey bar). Results are presented as mean±SEM from 15 controls and 16 RA patients. (B) Quantification of DNA-PKcs, pDNA-PKcs, Ku70 and Ku80 protein levels by Western blotting in cells harvested after 72 h. (C) Relative expression levels of the four proteins were quantified by measuring band intensities adjusted by β-actin and are shown as mean±SEM for 6 RA patients and 6 control donors. (D) Correlation of DNA-PKcs expression with DNA damage. CD4$^+$CD45RO$^-$ T cells from three RA donors were treated with the indicated doses of $H_2O_2$ for 1 h, and DNA damage was assayed by comet assay. DNA-PKcs mRNA expression was quantified by qPCR. (E) Correlation of DNA-PKcs expression with DNA damage. Transcript levels of DNA-PKcs from 16 RA samples were quantified by qPCR and standardized by 18S ribosomal RNA; DNA damage was assayed by comet assay.
Figure 4:
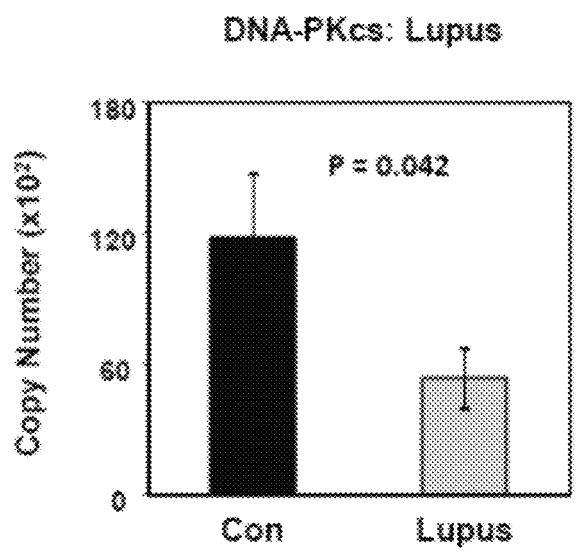
FIG. 4. DNA-PKcs expression is down regulated in SLE CD4 T cells. CD4+CD45RO−T cells were purified from SLE patients and age-matched controls. Cells were analyzed immediately after isolation. (B) Transcript levels of DNA-PKcs from freshly isolated control (n=11) and SLE samples (n=13) were quantified by qPCR and standardized by 18S ribosomal RNA. Data are presented as mean±SEM.

Besides ATM and ATR, the PI3K-related enzyme DNA-PKcs is an important player amongst the DNA damage sensors. To implicate this enzyme in regulating the fate of resting naïve T cells, DNA-PKcs transcript and protein levels were measured in naïve CD4 T cells from healthy control donors and RA patients (FIG. 3). Expression of DNA-PKcs specific sequences in T cell extracts were increased 1.4-fold in the freshly isolated RA samples (FIG. 3A, p=0.04). Spontaneous upregulation was a disease-specific finding. CD4 T cells isolated from patients with active SLE had significant lower transcript levels for DNA-PKcs than controls (FIG. 4, p=0.04). Also, RA T cells contained significantly higher concentrations of DNA-PKcs protein (FIG. 3A, B). Western blotting confirmed that RA T cells contained higher amounts of phosphorylated DNA-PKcs (FIG. 3B, C). The kinase is only one of the core elements of the NHEJ repair complex and needs to partner with Ku70/80, a heterodimer critically involved in detecting DSB. Quantification of Ku70 and Ku80 protein revealed a statistically significant reduction in RA T cells compared to control T cells to about half of the levels (FIG. 3C; p+0.05 for Ku70 and p=0.02 for Ku80).

To link increased DNA-PKcs expression with the cellular burden of damaged DNA, tail moments and DNA-PKcs transcript concentrations were compared in individual T-cell samples (FIG. 3D). The higher the T cells' tail moments, the more intense the induction of DNA-PKcs transcription. In an alternative approach, T cells were exposed to exogenous genotoxic stress and induction of DNA-PKcs was monitored. Tail moments tripled as the T cells were exposed to increasing concentrations of $H_2O_2$. Transcript levels of DNA-PKcs increased linearly, suggesting swift reactivity of this enzyme system to DNA fragmentation in T cells (FIG. 3E).

In essence, naïve RA T cells are characterized by an imbalance of the core elements of the NHEJ complex, with overexpression and activation of DNA-PKcs and underrepresentation of Ku70 and Ku80.

Inhibition of DNA-PKcs Activity and Silencing of DNA-PKcs Restores Apoptotic Resistance in RA T Cells.

Figure 5:
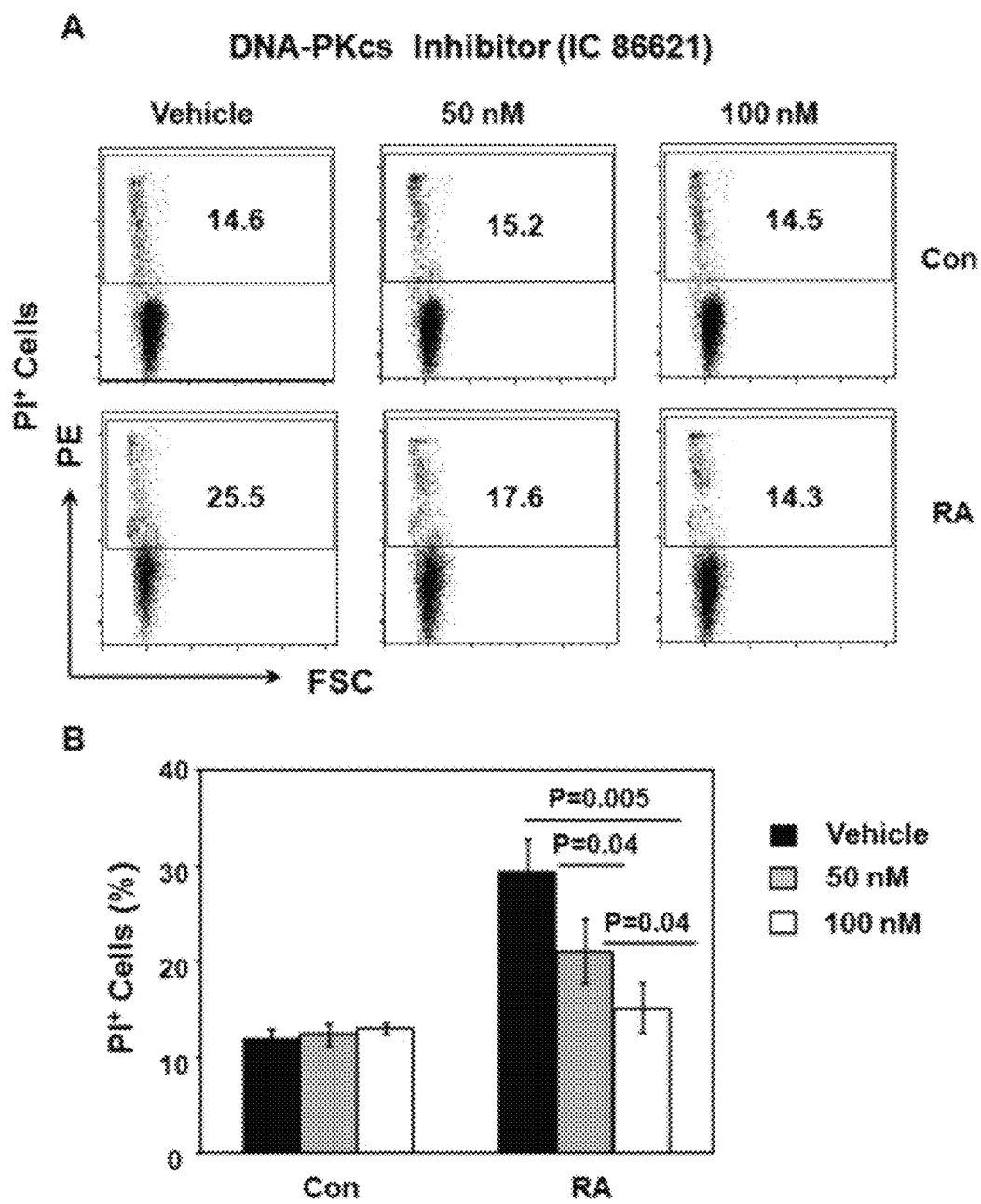
FIG. 5. Inhibition of DNA-PKcs activity protects RA T cells from apoptosis. CD4+CD45RO− T cells were isolated from 6 control donors and 7 RA patients. Cells were maintained in culture without stimulation for 48 h and then were treated with the DNA-PKcs inhibitor IC86621 (50 nM, 100 nM) or vehicle for 24 h. Cells were harvested and (A) T-cell apoptosis was measured by flow cytometry staining for PI. Representative cytometric data from one patient and one control are shown. (B) Frequencies of PI-positive T-cells in the absence and presence of the DNA-PKcs inhibitor from 6 controls and 7 RA patients are presented as mean±SEM.

To implicate DNA-PKcs directly in rendering RA T cells apoptosis susceptible, control and RA T cells were treated with the DNA-PKcs inhibitor IC86621, and their apoptotic response pattern was quantified by flow cytometry measurement of PI-positive T cells (FIG. 5A, B). The DNA-PKcs inhibitor essentially did not affect survival in control T cells. After 72 h of ex vivo culture 12-14% of the control T cells were apoptotic, independent from treatment with the DNA-PKcs inhibitor. In contrast, inhibition of the enzymatic activity of DNA-PKcs improved survival rates among RA T cells. Doses of 100 nM were sufficient to normalize apoptotic susceptibility and reduced the proportion of PI-positive cells to levels seen in the control T cells. The protection of RA T cells from apoptosis was dose-dependent (FIG. 5B) suggesting that DNA-PKcs-dependent signaling pathways are dominant in regulating life-death decisions in these T cells. DNA-PKcs appears to be less relevant in normal T cells as DNA-PKcs inhibition had essentially no effects.

In an alternative approach, the function of DNA-PKcs was inhibited by siRNA interference. By transfecting RA T cells with DNA-PKcs specific-interfering sequences, transcript levels for the gene were reduced by about 70% (FIG.

Figure 6:
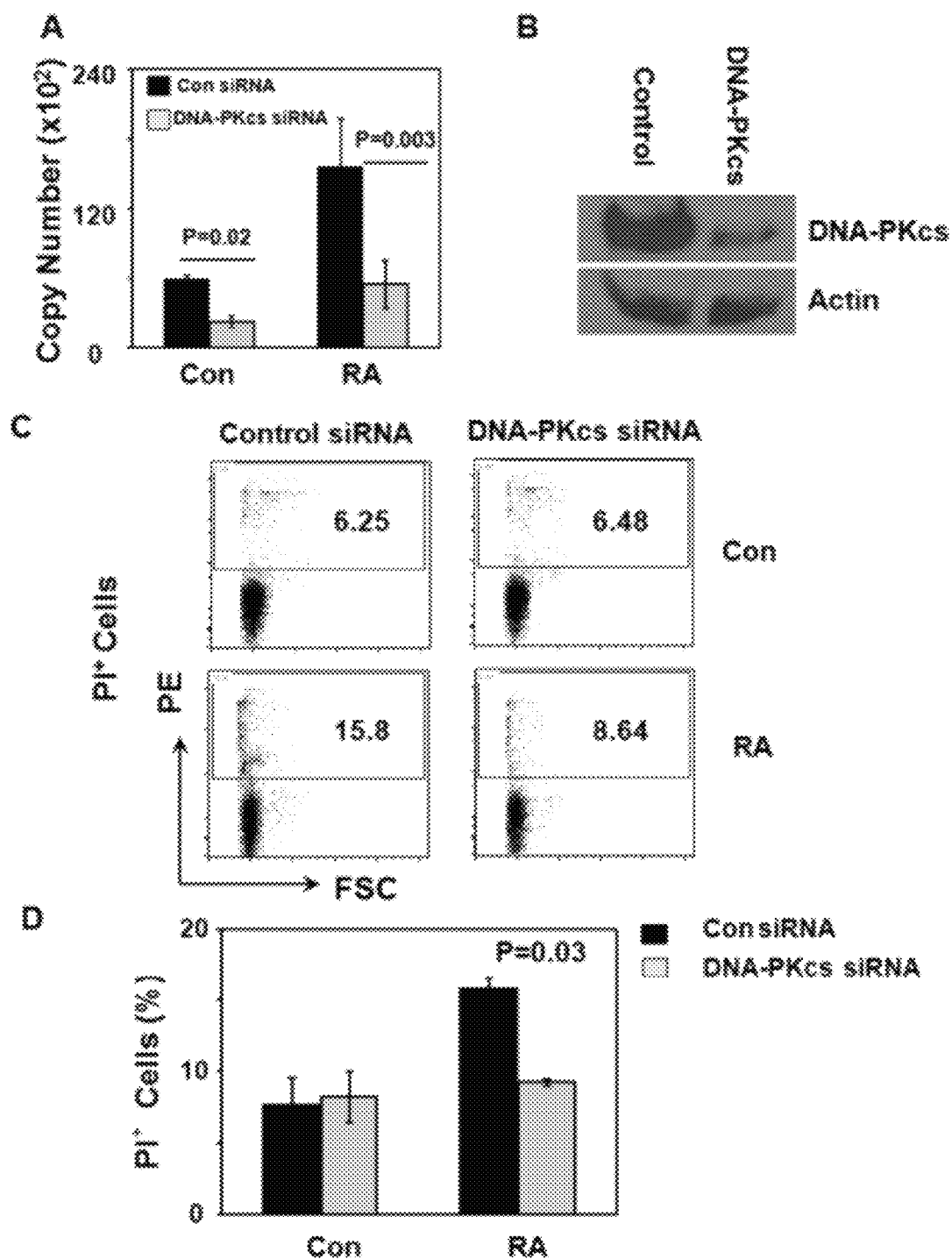
FIG. 6. Silencing of the DNA-PKcs gene reduces apoptosis in RA T cells. CD4+CD45RO− T cells were purified from 3 control donors and 3 RA patients and transfected with control or DNA-PKcs specific siRNA oligonucleotides by nucleofection. (A, B) Twenty-four hours after transfection, DNA-PKcs transcript levels were quantified by qPCR, and DNA-PKcs protein levels were detected by Western blotting. (C) T-cell apoptosis was analyzed by staining for PI.

6A). Western blotting confirmed that RNA interference was able to depress protein levels markedly (FIG. 6B). Reduction of DNA-PKcs levels had immediate consequences for the propensity of naïve CD4 T cells to undergo apoptosis (FIG. 6C, D). The rates of PI-positive T cells diminished from 15.76% in populations with intact DNA-PKcs to 9.27% in T cells with silenced DNA-PKcs (FIG. 6D, p=0.03).

These experiments directly involved the DNA-damage sensing enzyme DNA-PKcs in setting the apoptotic threshold in RA T cells.

Inhibition of the JNK Pathway Protects RA T Cells from Cell Death.

Since levels of phosphorylated p53 are decreased in RA T cells (see FIG. 2), it was important to understand how DNA-PKcs activates the cell death machinery. A screening approach with a panel of signal pathway inhibitors was applied to pinpoint which of these pathways has a role in transmitting death signals (FIG. 7A). As expected, inhibiting survival signals transmitted by the NF-κB and the AKT pathway increased T cell death rates. Only one of the inhibitors, blocking the functional activity of JNK was able to protect RA T cells from dying. Dose-response experiments demonstrated that inhibiting JNK activity could normalize the death rate and that 10 µM JNK inhibitor II were more effective than 5 µM (FIG. 7B, C).

To confirm overactivation of the JNK signaling pathway, naïve CD4 T cells from RA patients were isolated and, immediately following isolation, analyzed for the spontaneous expression of pJNK. Cytometric analysis confirmed higher expression of pJNK in freshly isolated CD4 T cells from RA patients compared to control T cells. Sustained and spontaneous signaling activity of the JNK pathway was confirmed after 72 h of maintaining T cells in culture, a stressor that upregulates T cell death rate significantly (FIG. 7D, E). FACS analysis demonstrated strong expression of pJNK in a subset of T cells, forming a shoulder in the histograms (FIG. 7D). MFI of pJNK was more than doubled in the patient-derived T cells (FIG. 7E). Western blotting of cell protein extracts confirmed that pJNK was expressed at significantly higher concentrations in RA T cells (FIG. 7G, H). In patient-derived T cells, the band intensities for both pJNK1 and pJNK2 were consistently higher (p=0.0005 and p=0.04), supporting the concept that the JNK signaling pathway is spontaneously activated in RA patients.

To establish a link between the induction of the DNA damage sensing enzyme DNA-PKcs and the increased baseline activation of JNK signaling, DNA-PKcs was knocked down by siRNA interference in RA T cells. Forced reduction in DNA-PKcs (FIG. 7I) was accompanied by a marked loss in JNK phosphorylation.

Activation of the DNA-PKcs-JNK Pathway in RA T Cells Induces the Proapoptotic BH3-Only Proteins Bim and Bmf.

Spontaneous upregulation of the DNA-PKcs-JNK pathway in RA T cells indicated continuous DNA repair activity that activates cell-internal stress kinases and jeopardizes T-cell survival. Stress-induced apoptosis mostly involves triggering of the intrinsic cell death machinery, employing BH3-only members of the Bcl-2 protein family as essential initiators of apoptotic cell death. BH3-only proteins, including Bim, Bmf, Noxa, Puma, Bad, and Bid are thought to unleash Bax/Bak-like proteins from their sequestration by prosurvival Bcl-2 family members to eventually facilitate the release of apoptogenic molecules, such as cytochrome c and downstream activation of caspases.

To understand how activation of DNA-PKcs and JNK renders resting RA T cells susceptible to apoptosis, production of Puma, Noxa, Bim and Bmf was assessed (FIG. 8A). In freshly isolated T cells from RA patients and controls, transcript levels of Puma and Noxa were indistinguishable, but levels of Bim and Bmf specific sequences were almost doubled in the patient-derived cells. These data were confirmed by flow cytometry analysis of Bim and Bmf protein (FIG. 8B, C). Expression of the proapoptotic protein Bim as well as Bmf was significantly higher in RA T cells. There was a tendency for RA T cells to contain lower levels of Bcl-2 protein (FIG. 8D), which did not reach statistical significance.

To examine whether the overexpression of Bim protein was mechanistically connected to the upregulation of DNA-PKcs and JNK, RA T cells were treated with the DNA-PKcs inhibitor IC 86621 or the JNK inhibitor II. Bim and Bmf protein concentrations were compared in treated and untreated T cells by flow cytometry (FIG. 8E, F, G, H). Pharmacologic blockade of DNA-PKcs activity or inhibition of the JNK pathway both reduced intracellular Bim and Bmf levels, supporting a direct connection between DNA-PKcs-JNK upregulation and BH3 protein-mediated apoptotic susceptibility.

These data suggested that Puma and Noxa are uninvolved in the shortened survival of RA T cells; rather, the internal apoptosis machinery responds to the cell's failure to repair DNA by upregulating Bim, shifting the Bim:Bcl-2 ratio and rendering T cells apoptosis susceptible.

Discussion

In rheumatoid arthritis, the process of immune aging is accelerated. RA patients accumulate CD4+ T cells that have lost expression of CD28 and utilize alternate co-stimulatory molecules to sustain pro-inflammatory functions in peripheral tissues (Park W, et al. (1997) Eur J Immunol 27(5): 1082-1090; Schmidt D, et al. (1996) J Clin Invest 97(9): 2027-2037; Weyand C M, et al. (1997) Med Clin North Am 81(1): 29-55; Weyand C M and Goronzy J J (2006) Nat Clin Pract Rheumatol 2(4): 201-210). Molecularly, RA T cells are distinct in that they have an intrinsic deficiency of two enzymes implicated in maintaining genomic stability: the telomere-elongating enzyme telomerase, and ATM, a kinase critically involved in recognizing and repairing DNA DSB (Fujii H, et al. (2009) Proc Natl Acad Sci USA 106(11): 4360-4365; Shao L, et al. (2009) J Exp Med 206(6): 1435-1449). The current study has examined whether chronic DNA damage activates alternative pathways in DNA surveillance and repair activity and how deficiencies in DNA repair and telomere repair affect T cell survival. The study focused on naïve and resting CD4 T cells as they represent the reserve pool of the immune system and their survival critically affects the process of immune aging. Such naïve CD4 T cells were found to be apoptosis susceptible, to accumulate damaged DNA and to upregulate DNA-PKcs phosphorylation. The induction of DNA-PKcs in RA T cells was combined with a reduction in Ku70 and Ku80 protein, causing a dysbalance of core components of the NHEJ complex. Nevertheless, the overexpression of DNA-PKcs had profound functional consequences; inhibition of enzyme activity protected T cells from apoptotic death. DNA-PKcs-dependent apoptosis was mediated through the stress kinase signaling pathway, specifically involving JNK. RA T cells expressed increased amounts of the apoptogenic BH3-only proteins Bim and Bmf and blockade of either DNA-PKcs or JNK activity normalized T cell death rates.

Mechanisms of T-cell apoptosis have been implicated in the formation of the T cell repertoire and in T cell autoimmunity. Yet, studies have concentrated on antigen-experienced memory T cells and antigen-induced clonal expansion. How T-cell death is regulated in the pool of peripheral naïve T cells, the host's lymphocyte reserve, was unclear. Antigen-naïve T cells are Fas resistant and need to be restimulated and acquire memory T cell features before they can die through the Fas-FasL pathway (Miyawaki T, et al. (1992) J Immunol 149(11): 3753-3758). The current study implicates the sensing of damaged DNA in the regulation of T cell survival. In RA T cells, DNA-PKcs becomes an important regulator of T cell longevity. Apoptotic loss of T cells was normalized when enzyme activity was blocked.

T cells require growth factors to stay alive and to repopulate the T cell pool through homeostatic proliferation. Naïve T cells require IL-7 and, in humans, respond to IL-15 as a homeostatic cytokine. The pool of naïve T cells persistently expresses the low-affinity receptor for IL-2 (Ma A, et al. (2006) Annu Rev Immunol 24: 657-679; Surh C D, et al. (2008) Immunity 29(6): 848-862). T cells closely monitor the availability of such growth and survival factors and cytokine deficiency activates intracellular sensors, such as FOXO3A (Dijkers P F, et al. (2000) Curr Biol 10(19): 1201-1204). However, supplementation of growth-promoting cytokines, including the homeostatic cytokines IL-2, IL-7 and IL-15, could not rescue naïve human T cells from dying whereas inhibition of DNA-PKcs as well as JNK was able to reset the apoptotic threshold. These findings implicate the DNA-PKcs-JNK pathway in the regulation of T cell homeostasis and the long-term health of the immune system.

Interestingly, both ATM and DNA-PKcs have a role in regulating T cell fate. Resting healthy T cells died predominantly through activating ATM (FIG. 2) whereas RA T cells lack availability of that mechanism and seem to resort to alternative means of DNA surveillance. Besides the repression of ATM transcription, RA T cells also produce low amounts of p53 (Shao et al, 2009). The tumor repressor p53 is well known for its role in cellular responses to DNA breaks, with double-strand breaks the most powerful lesion to activate p53-dependent apoptosis. Broken DNA initiates recruitment of ATM which rapidly phosphorylates p53, leading to its stabilization, induction of downstream transcriptional targets and cell-cycle arrest or apoptosis (Shiloh Y (2003) Nat Rev Cancer 3(3): 155-168; Vousden K H, et al. (2002) Nat Rev Cancer 2(8): 594-604). p53 is so important that p53-deficient cells fail to respond to this cell cycle checkpoint (Brown J M, et al. (2005) Nat Rev Cancer 5(3): 231-237; Maclean K H, et al. (2008) J Clin Invest 118(1): 79-88). Yet, data presented here strongly support the notion that under conditions of p53 deficiency T cells are able to employ DNA-PKcs-mediated activation of stress kinases to access the endogenous cell death machinery. Knockdown of DNA-PKcs promptly reduced JNK phosphorylation, establishing a mechanistic link between the two signaling networks (FIG. 7).

An intriguing result of the current study is the dysbalance of DNA-PKcs and Ku70/80. Under physiologic conditions, DNA-PKcs is only recruited to DNA ends after the Ku70/80 heterodimer has bound DNA ends (Smith G C, et al. (1999) Biochem Soc Symp 64: 91-104). DNA-PK synapses the ends and removes the overhanging 3' and 5' ends to allow for rejoining by DNA ligase (DeFazio L G, et al. (2002) EMBO J. 21(12): 3192-3200; Lees-Miller S P, et al. (2003) Biochimie 85(11): 1161-1173; Spagnolo L, et al. (2006) Mol Cell 22(4): 511-519). An interesting scenario emerges in RA T cells. Only the catalytic subunit of the enzyme is activated, whereas Ku70/Ku80 remain low, undermining the cell's options to proceed with DNA end joining. Under these conditions chronically induced catalytic subunit of DNA-PK ultimately harms the cell and mediates T cell apoptosis. Thus, coordinated regulation of both DNA-PKcs and Ku70/Ku80 may be necessary to facilitate successful repair of DNA lesions. DNA-PKcs alone, however, may be sufficient to trigger other signaling pathways, e.g. the JNK pathway to regulate cellular functions (Damrot J, et al. (2009) J Mol Biol 385(5): 1409-1421; Fritz G, et al. (2006) Mol Biol Cell 17(2): 851-861). These findings suggest that in human T cells DNA-PK activation is possible, even when expression of the Ku70/Ku80 heterodimer is low, broadening the role of the enzyme in cellular regulation.

Data collected in this study provide detailed information that sensing of damaged DNA by DNA-PK initiates an integrated pathway, with activation of the JNK signaling network and, eventually, engagement of the intrinsic apoptosis machinery. Expression studies indicated selectivity in this process as Bim and Bmf were expressed at higher levels in apoptosis-sensitive RA T cells and their levels normalized when the DNA-PKcs-JNK axis was blocked (FIG. 8). Proteins of the Bcl-2 family, including the prosurvival members Bcl-2, Bcl-xL, Bcl-w, and Mcl-10 and the prodeath Bax/Bak-like proteins ultimately control cell survival and response patterns to apoptotic stressors. The BH3-only proteins Bad, Bik, Bid, Bim, Bmf, Puma, and Noxa are essential apoptotic initiators (Dania) N N, et al. (2004) Cell 116(2): 205-219), yet each of them may respond to particular cellular stressors. Bim has emerged as critical in apoptosis following withdrawal of cytokines and is necessary in the deletion of autoreactive murine T cells (Bouillet P, et al. (2002) Nature 415(6874): 922-926; Enders A, et al. (2003) J Exp Med 198(7): 1119-1126). Bim has also been implicated in regulating the downregulation of T cell responses as immune activation subsides (Hildeman D A, et al. (2002) Immunity 16(6): 759-767; Pellegrini M, et al. (2003) Proc Natl Acad Sci USA 100(24): 14175-14180). Puma and Noxa are recognized as p53-induced apoptosis regulators and have been connected to both cytokine-deprivation and DNA damage-induced apoptosis (Ekert P G, et al. (2006) Blood 108(5): 1461-1468; Jeffers J R, et al. (2003) Cancer Cell 4(4): 321-328; Shibue T, et al. (2003) Genes Dev 17(18): 2233-2238; Villunger A, et al. (2003) Science 302(5647): 1036-1038). Studies of Bid deficiency have produced controversial results (Kaufmann T, et al. (2007) Cell 129(2): 423-433; Kaufmann T, et al. (2007) Cell 129(2): 423-433) with a recent report that could not confirm increased genomic instability and leukemogenesis upon mitomycin treatment (Kaufmann T, et al. (2007) Cell 129(2): 423-433) removing Bid as a candidate for monitoring DNA damage in healthy and RA T cells. Gene expression screening focused attention onto Bim and Bmf, compatible with the p53 independence of the apoptosis.

Bim and Bmf share subcellular localization and activation mechanisms. Under nonapoptotic conditions, Bim and Bmf are sequestered via dynein light chains to the actin and tubulin cytoskeleton, respectively, which keeps them from activating Bak and Bax (Puthalakath H, et al. (1999) Mol Cell 3(3): 287-296; Puthalakath H, et al. (2001) Science 293(5536): 1829-1832). Cell stress signals activate Bim and Bmf through phosphorylation within their dynein binding sites, mobilizing both proteins from the cytoskeleton and making them available to cause conformational changes within Bak and Bax, enabling them to homooligomerize and forming pores in the outer mitochondrial membrane (Antonsson B, et al. (2001) J Biol Chem 276(15): 11615-11623; Wei M C, et al. (2000) Genes Dev 14(16): 2060-2071). JNK has been proposed to mediate Bim and Bmf phosphorylation (Lei K, et al. (2003) Proc Natl Acad Sci USA 100(5): 2432-2437; Tianhu Z, et al. (2009) Mol Biol Rep), possibly releasing them from their cytoskeletal sequestration. Pharmacologic inhibition of either JNK or of DNA-PKcs normalized the levels of Bim as well as Bmf in the patient-derived T cells, localizing activation of DNA-PKcs and JNK upstream of the intrinsic apoptosis machinery.

A most interesting aspect of the present work is how it can impact the understanding of the autoimmune syndrome RA and current therapeutic approaches. Chronic T cell loss, particularly in the naïve compartment, will elicit homeostatic control mechanisms, restoring T cell numbers by enforced autoproliferation. Thus, the T cell pool in RA patients is under high turnover, eventually jeopardizing the proliferative reserve needed for immune competence. So far, RA has not been regarded as a syndrome of chronic lymphopenia (Weyand C M, et al. (2003) Exp Gerontol 38(8): 833-841). Yet, constant leaking of T cells and widespread DNA damage in surviving T cells must have consequences for the composition of the T cell repertoire and the functional competency of individual T cells. Ideally, damaged DNA could be repaired and nuclear stability maintained to ensure optimal survival time and prevention of cellular senescence. Enhancing production of the DNA-PK subunits Ku70/Ku80 may have beneficial effects in counteracting T cell loss in RA. Alternatively, as evidenced by this study, inhibiting chronically activated DNA-PKcs protects RA T cells from apoptosis and thus should be considered as a therapeutic intervention. In the current study, protection from the induction of the apoptogenic mediators Bim and BMF could be achieved with either inhibiting DNA-PKcs activity or blocking JNK (FIG. 8). Thus, either intervention could be explored as a new strategy to prolonging the survival of naïve CD4 T cells. Downregulation of JNK activity may have additional anti-inflammatory effects (Bennett B L, et al. (2001) Proc Natl Acad Sci USA 98(24): 13681-13686). Targeting DNA-PKcs, however, would exploit the most upstream component of the DNA-PK-JNK axis. The DNA-PKcs inhibitor used in the current study displays high specificity for this kinase. In previous reports concentrations of up to 100 µM have shown neither activity against distantly related protein kinases (protein kinase A, protein kinase C, checkpoint protein kinase 1, cyclin-dependent kinase 2, Rous sarcoma tyrosine kinase, aurora-related kinase 2 and casein kinase 1) nor against the closely related protein kinases ATR and ATM (Kashishian A, et al. (2003) Mol Cancer Ther 2(12): 1257-1264). Here, T cell survival was improved at doses 1000-fold lower (50-100 nM).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of increasing the viability or diversity of unprimed lymphocytes in an individual having rheumatoid arthritis, the method comprising: contacting unprimed lymphocytes of the individual with an effective amount of an agent that inhibits DNA-dependent protein kinase catalytic subunit (DNA-PKcs)-directed apoptosis, wherein the agent that inhibits DNA-PKcs-directed apoptosis is an inhibitor of DNA-PKcs, wherein the viability and diversity of unprimed lymphocytes is increased following the contacting relative to prior to the contacting, and wherein the agent is 1-(2-hydroxy-4-morpholin-4-yl-phenyl)ethanone.

2. The method according to claim 1, wherein the agent is administered to the unprimed lymphocytes in vivo.

3. The method according to claim 1, wherein the agent is administered to the unprimed lymphocytes ex vivo.

4. The method according to claim 1, wherein the method further comprises the step of measuring the number of unprimed lymphocytes in the individual following the contacting.

5. The method according to claim 1, wherein the agent is co-administered with a therapy to treat the Rheumatoid Arthritis.

6. The method according to claim 1, wherein the individual is a bone marrow transplant recipient.

7. The method according to claim 1, wherein the individual is 65 years old or older.

8. The method according to claim 1, wherein the unprimed lymphocytes are negative for CD25.

9. A method for reducing unprimed T lymphocyte apoptosis in an individual having rheumatoid arthritis, the method comprising: contacting unprimed T lymphocytes of the individual with an effective amount of an agent that inhibits DNA-dependent protein kinase catalytic subunit (DNA-PKcs)-directed apoptosis, wherein the agent that inhibits DNA-PKcs-directed apoptosis is an inhibitor of DNA-PKcs, wherein unprimed T lymphocyte apoptosis is reduced following the contacting relative to prior to the contacting, and wherein the agent is 1-(2-hydroxy-4-morpholin-4-yl-phenyl)ethanone.

10. The method according to claim 9, wherein the T lymphocytes are unprimed CD4+ T lymphocytes.

11. The method according to claim 9, wherein the agent is administered to the unprimed T lymphocytes in vivo.

12. The method according to claim 9, wherein the agent is administered to the unprimed T lymphocytes ex vivo.

13. The method according to claim 9, wherein the agent is co-administered with a therapy to treat rheumatoid arthritis.

14. The method according to claim 9, wherein the unprimed lymphocytes are negative for CD25.

* * * * *